US010639283B2

(12) United States Patent
Haksar et al.

(10) Patent No.: US 10,639,283 B2
(45) Date of Patent: May 5, 2020

(54) GASTRIC RESISTANT PHARMACEUTICAL OR NUTRACEUTICAL COMPOSITION WITH RESISTANCE AGAINST THE INFLUENCE OF ETHANOL

(71) Applicant: Evonik Operations GmbH, Essen (DE)

(72) Inventors: Priyanka Bansilal Haksar, Thane (West) (IN); Shraddha Sanjeev Joshi, Navi Mumbai (IN); Harsh Shah, Ahmedabad (IN); Preeti Patil, Mumbai (IN); Smitha Shetty, Mumbai (IN)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 14/416,500

(22) PCT Filed: Oct. 18, 2012

(86) PCT No.: PCT/EP2012/070639
§ 371 (c)(1),
(2) Date: Jan. 22, 2015

(87) PCT Pub. No.: WO2014/032741
PCT Pub. Date: Mar. 6, 2014

(65) Prior Publication Data
US 2015/0209298 A1  Jul. 30, 2015

(30) Foreign Application Priority Data
Aug. 27, 2012  (IN) .......................... 3531/CHE/2012

(51) Int. Cl.
| A61K 9/50 | (2006.01) |
| A61K 9/28 | (2006.01) |
| A61K 31/4439 | (2006.01) |
| A61K 31/522 | (2006.01) |
| A61K 31/135 | (2006.01) |
| A61K 31/138 | (2006.01) |
| A61K 31/381 | (2006.01) |

(52) U.S. Cl.
CPC ............ *A61K 9/5073* (2013.01); *A61K 9/286* (2013.01); *A61K 9/2846* (2013.01); *A61K 9/2886* (2013.01); *A61K 9/2893* (2013.01); *A61K 9/5026* (2013.01); *A61K 9/5036* (2013.01); *A61K 9/5047* (2013.01); *A61K 9/5089* (2013.01); *A61K 31/135* (2013.01); *A61K 31/138* (2013.01); *A61K 31/381* (2013.01); *A61K 31/4439* (2013.01); *A61K 31/522* (2013.01)

(58) Field of Classification Search
None
See application file for complete search history.

(56) References Cited

U.S. PATENT DOCUMENTS

| 6,365,148 | B1 | 4/2002 | Kim et al. |
| 2007/0071821 | A1* | 3/2007 | Young ............................ 424/470 |
| 2008/0107732 | A1 | 5/2008 | Dharmadhikari et al. |
| 2009/0196889 | A1* | 8/2009 | Penhasi ................ A61K 9/2013 424/400 |
| 2010/0129445 | A1* | 5/2010 | Asmussen et al. ........... 424/468 |
| 2010/0234442 | A1* | 9/2010 | Duarte-Vazquez .......................... A61K 9/2054 514/423 |
| 2012/0093926 | A1 | 4/2012 | Bodinge et al. |
| 2015/0190348 | A1 | 7/2015 | Haksar et al. |

FOREIGN PATENT DOCUMENTS

| CN | 1276009 A | 12/2000 |
| JP | 2002-505251 A | 2/2002 |
| JP | 2010-522742 A | 7/2010 |
| JP | 2010-529056 A | 8/2010 |
| KR | 10-1999-0032308 | 5/1999 |
| WO | 2005 101983 | 11/2005 |
| WO | 2012 022498 | 2/2012 |
| WO | 2012 077038 | 6/2012 |

OTHER PUBLICATIONS

Written Opinion of the International Searching Authority dated Mar. 20, 2013 in PCT/EP12/070639 Filed Oct. 18, 2012.
International Search Report dated Mar. 20, 2013 in PCT/EP12/070639 Filed Oct. 18, 2012.
U.S. Appl. No. 14/416,171, filed Jan. 21, 2015, US2015/0190348 A1, Haksar, etal.
Office Action (Notification of Reasons for Refusal) dated Jul. 19, 2016 in Japanese Patent Application No. 2015-528887 with English translation.
Office Action dated Apr. 15, 2016 in Chinese Patent Application No. 201280074955.0 with English translation.
U.S. Appl. No. 15/117,062, filed Aug. 5, 2016, US2016/0354319 A1, Joshi et al.

\* cited by examiner

*Primary Examiner* — Robert A Wax
*Assistant Examiner* — Randeep Singh
(74) *Attorney, Agent, or Firm* — Grüneberg and Myers PLLC

(57) ABSTRACT

A pharmaceutical or nutraceutical composition with a core, an inner layer, and an outercoating layer, wherein a pharmaceutical or a nutraceutical active ingredient is contained in the core, at least 30% by weight of a salt of alginic acid is contained in the inner layer, and at least 30% by weight of a polymer or copolymer with anionic side groups is contained in the outer coating layer.

17 Claims, No Drawings

US 10,639,283 B2

GASTRIC RESISTANT PHARMACEUTICAL OR NUTRACEUTICAL COMPOSITION WITH RESISTANCE AGAINST THE INFLUENCE OF ETHANOL

TECHNICAL BACKGROUND

US 2007/0104789 A1 describes gastro-resistant and ethanol-resistant controlled-release formulations comprising hydromorphone. The gastro-resistant and ethanol-resistant can be used in a matrix as well as the coating of the formulations. Alginic acid is mentioned among the examples for suitable gastro-resistant and-ethanol resistant substances. Pellet cores or granules may be prepared by anhydrous granulation, may be coated with the gastro-resistant and ethanol-resistant substances and then may be filled in capsules or bags or compressed into tablets under addition of dried pharmaceutical or nutraceutically acceptable auxiliary substances.

WO 2012/022498 describes a gastric resistant pharmaceutical or nutraceutical composition, comprising a core, comprising a pharmaceutical or nutraceutical active ingredient and a gastric resistant coating layer onto the core, wherein the release of the pharmaceutical or nutraceutical active ingredient is not more than 15% under in-vitro conditions at pH 1.2 for 2 hours in a buffered medium according to USP with and without the addition of 40% (v/v) ethanol, wherein the gastric resistant coating layer comprises 10 to 100% by weight of one or more salts of alginic acid with a viscosity of 30 to 720 cP of a 1% aqueous solution. The one layer system as described solves the problem protection against the influence of ethanol. However except for coatings which include the ammonium alginate, coatings which employ other alginate salts, like sodium or potassium alginate, show no resistance against the influence of calcium ions at the same time.

OBJECT OF THE INVENTION

Pharmaceutical or nutraceutical compositions are designed to release the active ingredient in a manner of reproducible release curves. This shall result in desirable and reliable blood level profiles which shall provide an optimal therapeutic effect. If the blood level concentrations are too low, the active ingredient will not cause a sufficient therapeutic effect. If the blood level concentrations are too high, this may cause toxic effects. In both cases non optimal blood level concentrations of an active ingredient can be dangerous for the patient and shall therefore be avoided. A problem exists in that the ideal ratios assumed for the release of active ingredient during the design of a pharmaceutical or nutraceutical composition can be altered by the general living habits, thoughtlessness or by addictive behaviour of the patients with respect to the use of ethanol or ethanol-containing drinks. In these cases, the pharmaceutical or nutraceutical form which is actually designed for an exclusively aqueous medium is additionally exposed to an ethanol containing medium of greater or lesser strength. Since health authorities like for instance the US Food and Drug Administration (FDA) focus more and more on the ethanol problem, ethanol resistance may be an important registration requirement in the near future.

Since not all patients are aware of the risk of simultaneous taking of a controlled release pharmaceutical or nutraceutical form and ethanol-containing drinks or do not follow or are not able to follow appropriate warnings, advice or recommendations, there is a demand for controlled release pharmaceutical or nutraceutical compositions, especially for gastric resistant pharmaceutical or nutraceutical compositions, such that their mode of action is affected as little as possible by the presence of ethanol.

Conventional gastric resistant pharmaceutical or nutraceutical compositions if coated or uncoated are usually not resistant to alcohol at all. Therefore one problem of the present invention was to provide gastric resistant pharmaceutical or nutraceutical compositions which are resistant against the influence of ethanol.

Especially there is a problem for gastric resistant or enteric formulated compositions. These kinds of formulations are usually coated with a gastric resistant coating layer (enteric coating layer) onto the core which has the function that the release of the pharmaceutical or nutraceutical active ingredient in the stomach, respectively at pH 1.2 for 2 hours according to USP, shall not exceed 10%, preferably less than 5%. This function ensures that acid-sensitive pharmaceutical or nutraceutical active ingredients are protected against inactivation and that pharmaceutical or nutraceutical active ingredients which may be irritate the stomach mucosa are not set free in too high amounts. On the other hand in many cases the release of the pharmaceutical or nutraceutical active ingredient in the intestine, respectively at pH 6.8 for one hour or less according to the USP method, is designed to exceed at least 70, 75% or more. The presence of ethanol in concentrations of 5, 10, 20 or 40% (volume/volume) in the gastric fluid usually leads to an increase to the release rates in the stomach. Due to distribution effect the effect of ingested ethanol is in the intestine not of that importance as in the stomach. Thus an effective protection against the influence of ethanol should prevent such an undesired increase of pharmaceutical or nutraceutical active ingredient in the stomach in the first place. Furthermore it may be desired that protection against the influence of ethanol shall at least not influence the comparably fast release rates at pH 6.8 in media without ethanol.

Salts of alginates are generally able to be cross linked via calcium ions in aqueous media and can build up hydro gel like structures. Thus active ingredient release profile of a pharmaceutical or nutraceutical composition which comprises salts of alginates may be influenced in a negative way in the presence of calcium ions. One further object of the present invention is to provide a pharmaceutical or nutraceutical composition with a release profile which is not or only slightly influenced in situations were considerable amounts of calcium ions are present in the food and are ingested together with the pharmaceutical or nutraceutical composition. This can for instance happen when diary products such like milk or yoghurt are consumed simultaneously. Surprisingly it has been found that the presence of calcium ion in USP buffer pH 6.8 has almost no influence on the release rate of coatings in which the inventive pharmaceutical or nutraceutical composition is used.

It was therefore an object of the present invention to provide a pharmaceutical or nutraceutical composition with a release profile which is show against the influence of ethanol at pH 1.2, release the active ingredient to an extent of at least 80% after 45 min at pH 6.8, preferably already at pH 5.5, and which is at the same time not or only slightly influenced in situations were considerable amounts of calcium ions are present in the food and are ingested together with the pharmaceutical or nutraceutical composition.

The objects are solved by a pharmaceutical or nutraceutical composition, comprising, comprising essentially or consisting of a) a core, comprising a pharmaceutical or a nutraceutical active ingredient and
b) an inner coating layer comprising at least 30% by weight of one or more salts of alginic acid and
c) an outer coating layer comprising at least 30% by weight of one or more polymers or copolymers comprising anionic side groups.

DETAILED DESCRIPTION OF THE INVENTION

The invention relates to a pharmaceutical or nutraceutical composition, comprising
a) a core, comprising a pharmaceutical or a nutraceutical active ingredient, and
b) an inner coating layer comprising at least 30, at least 40, at least 50, at least 60, at least 70, at least 80, at least 90% by weight of one or more salts of alginic acid and
c) an outer coating layer comprising at least 30, at least 40, at least 50, at least 60, at least 70, at least 80, at least 90% by weight of one or more polymers or copolymers comprising anionic side groups.

Gastric Resistant Pharmaceutical or Nutraceutical Composition

The pharmaceutical or nutraceutical composition as disclosed herein is a gastric resistant pharmaceutical or nutraceutical composition.

Gastric resistant shall mean that the release of the pharmaceutical or nutraceutical active ingredient is not more than 10%, not more than 8%, not more than 5% under in-vitro conditions at pH 1.2 for 2 hours in medium according to USP (for instance USP32).

Active Ingredient Release at pH 5.5

The release of the pharmaceutical or nutraceutical active ingredient is preferably at least 60, at least 75% under in-vitro conditions at pH 5.5 for 90, preferably 45 min in a buffered medium according to USP (for instance USP32).

Active Ingredient Release at pH 6.8 or 7.5

Preferably the release of the pharmaceutical or nutraceutical active ingredient is at least 75% under in-vitro conditions at pH 6.8 or at pH 7.5 for 45 min in a buffered medium according to USP (for instance USP32).

Many polymer coatings such as EUDRAGIT® L100-55 dissolve below pH 6.8 thus preferably the 75% release at pH 6.8 is the most relevant characteristic. However for polymer coatings which dissolve above pH 6.8 but below pH 7.5 like for instance the EUDRAGIT® S polymer type or the EUDRAGIT® FS polymer type, it is preferred that the release of the pharmaceutical or nutraceutical active ingredient is at least 75 under in-vitro conditions at pH 7.5 for 45 min in a buffered medium according to USP (for instance USP32).

Ethanol Resistant Pharmaceutical or Nutraceutical Composition

The pharmaceutical or nutraceutical composition as disclosed herein is an ethanol resistant pharmaceutical or nutraceutical composition.

Ethanol resistant shall mean that the enteric properties of the pharmaceutical or nutraceutical composition are maintained in the presence of certain amounts of ethanol.

Ethanol resistant shall mean that the release of the pharmaceutical or nutraceutical active ingredient is in the presence of ethanol not more than 10%, not more than 8%, not more than 5% to be measured under in-vitro conditions at pH 1.2 for 2 hours in medium according to USP with the addition of 5, 10, 20 or 40% (v/v) ethanol.

Calcium Resistant Pharmaceutical or Nutraceutical Composition

The pharmaceutical or nutraceutical composition as disclosed is a calcium resistant pharmaceutical or nutraceutical composition.

Calcium resistant shall mean that at least the enteric properties of the pharmaceutical or nutraceutical composition are maintained in the presence of certain amounts calcium ions.

Thus calcium resistant shall mean that the release of the pharmaceutical or nutraceutical active ingredient is not more than 10%, not more than 8%, not more than 5% under in-vitro conditions at pH 1.2 for 2 hours in medium according to USP (for instance USP32) with the addition of 1.25 mM calcium (or calcium ions respectively).

A preferred embodiment is that, after in-vitro conditions at pH 1.2 for 2 hours in medium according to USP (for instance USP32) with the addition of 1.25 mM calcium ions and after subsequent change to in-vitro conditions at pH 6.8 for 45 minutes in medium according to USP (for instance USP32) without the addition of calcium ions, the release of the pharmaceutical or nutraceutical active ingredient in % at a certain relapse time shall in the pH 6.8 medium with 1.25 mM calcium ions preferably differ by not more than plus/minus (+/−) 20%, not more than +/−15%, not more than +/−10% (the difference in % is always meant to be in absolute %).

Preferably the pharmaceutical or nutraceutical composition as disclosed shows enhanced calcium resistance. Enhanced calcium resistance shall mean that the active ingredient release properties of the pharmaceutical or nutraceutical composition at pH 6.8 are essentially maintained in the presence of certain amounts calcium ions.

Thus another preferred embodiment is that, after in-vitro conditions at pH 1.2 for 2 hours in medium according to USP (for instance USP32) with the addition of 1.25 mM calcium and after subsequent change to in-vitro conditions at pH 6.8 for 45 minutes in buffer medium according to USP (for instance USP32) with the addition of 1.25 mM calcium ions, compared to the same medium without the addition of calcium ions the release of the pharmaceutical or nutraceutical active ingredient in % at a certain release time shall preferably differ by not more than plus/minus (+/−) 20%, not more than +/−15%, not more than +/−10% (absolute % are meant).

The difference in % is always meant to be absolute %. Thus if the active ingredient release in the pH 6.8 medium without calcium is for instance 80%, the active ingredient release in the pH 6.8 medium with calcium shall be still in the range from 80 to 100% (+/−20% deviation).

Core

The core is comprising, comprising essentially, or consisting of a pharmaceutical or a nutraceutical active ingredient.

The core may comprise or may contain a neutral carrier pellet, for instance a sugar sphere or non-pareilles, on top of which the active ingredient may be bound in a binder, such as lactose, celluloses, like micro crystalline cellulose (MCC), or polyvinylpyrrolidon (PVP). In this case the active ingredient may be bound or placed localized at the surface of the core (as a part of the core). The binding of the active ingredient at the surface of the core in such a binding layer has usually no effect or influence in the sense of a release control function.

The core may alternatively comprise a pellet in the form of a polymeric matrix in which the active ingredient is bound. The core may comprise an uncoated pellet or granule consisting of a crystallized active ingredient. The core may be as well an active ingredient containing tablet, mini tablet or capsule. In these cases the active ingredient may be placed more or less randomly distributed throughout the core as a whole.

Coating Layers

The pharmaceutical or nutraceutical composition is comprising, comprising essentially or consisting of the core, the inner coating layer onto the core and the outer coating layer onto the inner coating layer.

The coating layers have the function of controlling the release of the active ingredient, which is placed in the core or at the surface of the core. The coating layers have also the function of providing resistance of the release rates against the presence ethanol or against the presence of calcium ions.

Preferably the pharmaceutical or nutraceutical composition is comprising, comprising essentially or consisting of the core, the inner coating layer and the outer coating layer and there are no further coating layers present, which would additionally control the release of the active ingredient.

The Inner Coating Layer

The inner coating layer is located onto the core. A sub coat may be located between the core and the inner coating layer. A sub coat may have the function to separate substances of the core from substances of the controlling layer which may be incompatible with each other. The sub coat has essentially no influence on the active ingredient release characteristics. Preferably there is no sub coat between the core and the inner coating layer. In this case the inner coating layer is in direct contact with core.

The total amount of the inner coating layer may be in the range of 2 to 90, 4 to 80 or 5 to 60% by weight in relation to the weight of the core.

The absolute amount of polymer the inner coating layer may be in the case of pellets or granules with a size in the range of 50 to 1000 μm (average diameter) in the range of 2 to 50, preferably 5 to 40 mg/cm$^2$.

The absolute amount of polymer in the inner coating layer may be in the case of tablets with a size in the range of more than 1 and up to 25 mm (Average diameter or length) in the range of 0.5 to 10, preferably 1 to 6 mg/cm$^2$.

The inner coating layer comprises at least 30, at least 40, at least 50, at least 60, at least 70, at least 80, at least 90% by weight of one or more salts of alginic acid.

The salts of alginic acid may be selected from sodium alginate, potassium alginate, magnesium alginate, lithium alginate or ammonium alginate or mixtures thereof.

The salts of alginic acid used for the inner coating layer may preferably have a viscosity of 30 to 720 cP of a 1% aqueous solution (weight/weight).

The inner coating layer may comprise up to 70, up to 60, up to 50, up to 40% by weight of pharmaceutical or nutraceutically acceptable excipients. The pharmaceutical or nutraceutically acceptable excipients in the inner coating layer are different from the salts of alginic acid. Preferably the inner coating layer comprises less than 10% by weight, less than 5% by weight, less than 1% by weight or any (0%) polymers or copolymers comprising anionic side groups.

A typical inner coating may for example comprise or contain 40-60% by weight of one or more salts of alginic acid and 40 to 60% by weight of a glidant, for instance talc.

The Outer Coating Layer

The outer coating layer is located onto the inner coating layer.

A sub coat may be located between the inner coating layer and outer coating layer. The sub coat has essentially no influence on the active ingredient release characteristics. Preferably there is no sub coat between the core and the inner coating layer. In this case the outer coating layer is in direct contact with the inner coating layer.

A top coat may be located on top of the outer coating layer. The top coat may be preferably water-soluble, essentially water-soluble or dispersible. A top coat may have the function of colouring the pharmaceutical or nutraceutical form or protecting from environmental influences for instance from moisture during storage. The top coat may consist out of a binder, for instance a water soluble polymer like a polysaccharide or HPMC, or a sugar compound like saccharose. The top coat may further contain pharmaceutical or nutraceutical excipients like pigments or glidants in high amounts. The topcoat has essentially no influence on the release characteristics. Preferably there is no top coat onto the outer coating layer.

The pharmaceutical or nutraceutical composition may be characterised in that there are except for the inner coating layer and the outer coating layer no further controlling layers present which control the release the pharmaceutical or a nutraceutical active ingredient.

The outer coating layer is comprising at least 30, at least 40, at least 50, at least 60, at least 70, at least 80, at least 90% or by weight of one or more polymers or copolymers comprising anionic side groups. Preferably the anionic side groups are carboxylic side groups.

The outer coating layer may comprise up to 60, up to 50, up to 40% by weight of pharmaceutical or nutraceutically acceptable excipients. The pharmaceutical or nutraceutically acceptable excipients in the outer coating layer are different from the polymers or copolymers comprising anionic side groups. Preferably the outer coating layer comprises less than 10% by weight, less than 5% by weight, less than 1% by weight or any (0%) salts of alginic acid.

A typical outer coating layer may for example comprise 30-50% by weight of one or more polymers or copolymers comprising anionic side groups, for instance EUDRAGIT® L100-55, 5 to 25% by weight of a plasticizer, for instance triethyl citrate (TEC), and 40 to 60% by weight of a glidant, for instance talc.

The total amount of the outer coating layer may be in the range of 2 to 90, 4 to 80 or 5 to 60% by weight in relation to the weight of the core.

The absolute amount of polymer the outer coating layer may be in the case of pellets or granules with a size in the range of 50 to 1000 μm (average diameter) in the range of 2 to 50, preferably 5 to 40 mg/cm$^2$.

The absolute amount of polymer in the outer coating layer may be in the case of tablets with a size in the range of more than 1 and up to 25 mm (Average diameter or length) in the range of 0.5 to 10, preferably 1 to 6 mg/cm$^2$.

Relation Inner/Outer Coating

The amount of the inner coating layer may be preferably at least equal or higher than the amount of the outer coating layer.

When the inner and the outer coating layer are calculated together as 100% the amount of the inner coating layer may be at least 50% by weight or more, at least 60% by weight or more, at least 70% by weight or more, at least 80% by weight or more, at least 90% by weight or more in relation to both coating layers.

Polymers or Copolymers Comprising Anionic Side Groups

The one or more polymers or copolymers comprising anionic side groups which may be preferably used for the outer coating layer may be selected from the group of (meth)acrylate copolymers or polyvinyl polymers or copolymers or celluloses. The anionic polymers or copolymers used for the outer coating are preferably not cross-linked. Anionic side groups are preferably carboxylic groups.

Anionic Celluloses

Suitable anionic polymer or copolymers may be carboxymethyl cellulose and its salts (CMC, Na-CMC, Blanose®, Tylopur®), carboxymethylethyl cellulose and its salts, cellulose acetate phthalate (CAP), cellulose acetate succinate (CAS), cellulose acetate trimelliate (CAT), hydroxypropyl methyl cellulose phthalate (HPMCP, HP50, HP55) or hydroxypropylmethyl cellulose acetate succinate (HPMCAS-LF, -MF, -HF).

Anionic Polyvinyl Polymers

Suitable polyvinyl polymers or copolymers may comprise structural units that are derived from unsaturated carboxylic acids other than acrylic acid or methacrylic acid as exemplified by polyvinylacetate-phthalate, a copolymer of vinylacetate and crotonic acid 9:1 or polyvinylacetate-succinate Anionic (Meth)Acrylate Copolymers The one or more polymers or copolymers comprising anionic side groups may comprise 25 to 95, preferably 40 to 95, in particular 60 to 40, % by weight free-radical polymerized $C_1$- to $C_{18}$-alkyl esters, preferably $C_1$- to $C_8$- or $C_1$- to $C_4$-alkyl esters alkyl esters of acrylic or of methacrylic acid and 75 to 5, preferably 60 to 5, in particular 40 to 60, % by weight (meth)acrylate monomers having an anionic side group, respectively a carboxylic side group.

The proportions mentioned normally add up to 100% by weight. However it is also possible in addition, without this leading to an impairment or alteration of the essential properties, for small amounts in the region of 0 to 10, for example 1 to 5, % by weight of further monomers capable of vinylic copolymerization, such as, for example, hydroxyethyl methacrylate or hydroxyethyl acrylate, to be present. It is preferred that no further monomers capable of vinylic copolymerization are present. $C_1$- to $C_4$-alkyl esters of acrylic or methacrylic acid are in particular methyl methacrylate, ethyl methacrylate, butyl methacrylate, methyl acrylate, ethyl acrylate and butyl acrylate.

A (meth)acrylate monomer having an anionic group, respectively a carboxylic side group, may be, for example, acrylic acid, with preference for methacrylic acid.

Examples for Suitable Anionic (Meth)Acrylate Copolymers

A suitable anionic (meth)acrylate copolymer may be comprising, essentially comprising, containing or consisting of polymerized units of
10 to 40% by weight of acrylic or methacrylic acid
10 to 80% by weight of a $C_4$- to $C_{18}$-alkyl ester of acrylic or methacrylic acid and optionally
0 to 60% by weight of another vinylic monomers without cross-linking side chains.

$C_4$- to $C_{18}$-alkyl ester of acrylic or methacrylic acid are preferably chosen from n-butyl methacrylate, 2-ethylhexyl acrylate, 2-ethylhexyl methacrylate, isodecyl methacrylate and lauryl methacrylate.

Another vinylic monomer is a vinylic monomer which is not acrylic or methacrylic acid or a $C_4$- to $C_{18}$-alkyl ester of acrylic or methacrylic acid. Another vinylic monomer may be preferably a $C_1$- to $C_3$-alkyl ester of acrylic or methacrylic acid, which are methyl acrylate, ethyl acrylate, propyl acrylate, methyl methacrylate, ethyl methacrylate or propyl methacrylate. Another vinylic monomer may be hydroxyethyl methacrylate, hydroxypropyl methacrylate, poly(ethylenglycol)methylether acrylat, poly(ethylenglycol) methylether methacrylat, poly(propylenglycol)methylether acrylat, poly(propylenglycol)methylether methacrylat or styrene.

Preferably the anionic (meth)acrylate copolymer is comprising, essentially comprising or containing polymerized units of
10 to 40% by weight of acrylic or methacrylic acid
10 to 50% by weight of ethyl acrylate
10 to 80% by weight of a $C_4$- to $C_{18}$-alkyl ester of acrylic or methacrylic acid and optionally
0 to 20 by weight of methyl methacrylate.

Preferably the anionic (meth)acrylate copolymer is comprising, essentially comprising or containing polymerized units of
20 to 40% by weight of methacrylic acid,
20 to 40% by weight of n-butyl methacrylate and
30 to 50% by weight of ethyl acrylate Preferably the anionic (meth)acrylate copolymer is comprising, essentially comprising or containing polymerized units of
20 to 40% by weight of methacrylic acid,
30 to 50% by weight of 2-ethylhexyl acrylate,
15 to 40% by weight of ethyl acrylate and optionally
0 to 20% by weight of methyl methacrylate.

Preferably the anionic (meth)acrylate copolymer is comprising, essentially comprising or containing polymerized units of
10 to 40% by weight of methacrylic acid,
20 to 70% by weight of 2-ethylhexyl methacrylate and
10 to 50% by weight of ethyl acrylate.

Preferably the anionic (meth)acrylate copolymer is comprising, essentially comprising or containing polymerized units of
20 to 40% by weight of methacrylic acid,
20 to 50% by weight of 2-ethylhexyl methacrylate and
20 to 50% by weight of ethyl acrylate.

Preferably the anionic (meth)acrylate copolymer is comprising, essentially comprising or containing polymerized units of
10 to 35% by weight of methacrylic acid,
40 to 70% by weight of 2-ethylhexyl methacrylate and
10 to 30% by weight of ethyl acrylate.

Preferably the anionic (meth)acrylate copolymer is comprising, essentially comprising or containing polymerized units of
20 to 40% by weight of methacrylic acid,
20 to 40% by weight of isodecyl methacrylate and
40 to 50% by weight of ethyl acrylate.

Preferably the anionic (meth)acrylate copolymer is comprising, essentially comprising or containing polymerized units of
20 to 40% by weight of methacrylic acid,
20 to 40% by weight of lauryl methacrylate and
30 to 50% by weight of ethyl acrylate.

Further Characteristics of the Anionic (Meth)Acrylate Copolymers,

Further characteristics of the anionic (meth)acrylate copolymer, especially of the anionic (meth)acrylate copolymers described above may be summarized as follows.

Preferably the (meth)acrylate copolymer may be characterized by a mean glass transition temperature from 25 to 120 or 40 to 80° C. (determined by DSC according to DIN EN ISO 11357).

Preferably the (meth)acrylate copolymer may be characterized by a minimum film forming temperature of 50° C. or less (determined according to DIN ISO 2115). Preferably the (meth)acrylate copolymer may be characterized by a mean molecular weight $M_w$ is 80.000 or more (determined by gel permeation chromatography, GPC).

Further Suitable Anionic (Meth)Acrylate Copolymer

Suitable anionic (meth)acrylate copolymers are those composed of 40 to 60% by weight methacrylic acid and 60 to 40% by weight methyl methacrylate or 60 to 40% by weight ethyl acrylate (EUDRAGIT® L or EUDRAGIT® L100-55 types). EUDRAGIT® L is a copolymer of 50% by weight methyl methacrylate and 50% by weight methacrylic acid. The pH of the start of the specific active ingredient release in intestinal juice or simulated intestinal fluid can be stated to be pH 6.0.

EUDRAGIT® L 100-55 is a copolymer of 50% by weight ethyl acrylate and 50% by weight methacrylic acid. EUDRAGIT® L30 D-55 is a dispersion comprising 30% by weight EUDRAGIT® L 100-55. The pH of the start of the specific active ingredient release in intestinal juice or simulated intestinal fluid can be stated to be pH 5.5. Likewise suitable are anionic (meth)acrylate copolymers composed of 20 to 40% by weight methacrylic acid and 80 to 60% by weight methyl methacrylate (EUDRAGIT® S type). The pH of the start of the specific active ingredient release in intestinal juice or simulated intestinal fluid can be stated to be pH 7.0.

Suitable (meth)acrylate copolymers are those consisting of 10 to 30% by weight methyl methacrylate, 50 to 70% by weight methyl acrylate and 5 to 15% by weight methacrylic acid (EUDRAGIT® FS type). The pH at the start of the specific active ingredient release in intestinal juice or simulated intestinal fluid can be stated to be pH 7.0.

EUDRAGIT® FS is a copolymer of 25% by weight methyl methacrylate, 65% by weight methyl acrylate and 10% by weight methacrylic acid. EUDRAGIT® FS 30 D is a dispersion comprising 30% by weight EUDRAGIT® FS.

Additionally suitable is a copolymer composed of
20 to 34% by weight methacrylic acid and/or acrylic acid,
20 to 69% by weight methyl acrylate and
0 to 40% by weight ethyl acrylate and/or where appropriate
0 to 10% by weight further monomers without cross-linking side chains
capable of vinylic copolymerization,
with the proviso that the glass transition temperature of the copolymer according to ISO 11357-2, subsection 3.3.3 (midpoint temperature $T_{mg}$), is not more than 60° C. This (meth)acrylate copolymer is particularly suitable, because of its good elongation at break properties, for compressing pellets to tablets.

Additionally suitable is a copolymer composed of
20 to 33% by weight methacrylic acid and/or acrylic acid,
5 to 30% by weight methyl acrylate and
20 to 40% by weight ethyl acrylate and
more than 10 to 30% by weight butyl methacrylate and where appropriate
0 to 10% by weight further monomers without cross-linking side chains capable of vinylic copolymerization, where the proportions of the monomers add up to 100% by weight,
with the proviso that the glass transition temperature of the copolymer according to ISO 11357-2, subsection 3.3.3 (midpoint temperature $T_{mg}$), is 55 to 70° C. Copolymers of this type are particularly suitable, because of its good mechanical properties, for compressing pellets to tablets.

The abovementioned copolymer is composed in particular of free-radical polymerized units of 20 to 33, preferably 25 to 32, particularly preferably 28 to 31% by weight methacrylic acid or acrylic acid, with preference for methacrylic acid, 5 to 30, preferably 10 to 28, particularly preferably 15 to 25% by weight methyl acrylate,
20 to 40, preferably 25 to 35, particularly preferably 18 to 22% by weight ethyl acrylate, and
more than 10 to 30, preferably 15 to 25, particularly preferably 18 to 22% by weight butyl methacrylate,
where the monomer composition is chosen so that the glass transition temperature of the copolymer is from 55 to 70° C., preferably 59 to 66, particularly preferably 60 to 65° C.

Glass transition temperature means in this connection in particular the midpoint temperature $T_{mg}$ according to ISO 11357-2, subsection 3.3.3. Measurement takes place without added plasticizer, with residual monomer contents (REMO) of less than 100 ppm, with a heating rate of 10° C./min and under a nitrogen atmosphere. The copolymer preferably consists essentially to exclusively of 90, 95 or 99 to 100% by weight of the monomers methacrylic acid, methyl acrylate, ethyl acrylate and butyl methacrylate in the ranges of amounts indicated above.

However, it is possible, without this necessarily leading to an impairment of the essential properties, for small amounts in the range from 0 to 10, e.g. 1 to 5% by weight of further monomers capable of vinylic copolymerization additionally to be present, such as, for example, methyl methacrylate, butyl acrylate, hydroxyethyl methacrylate, vinylpyrrolidone, vinylmalonic acid, styrene, vinyl alcohol, vinyl acetate and/or derivatives thereof.

Preparation of Anionic (Meth)Acrylate Copolymers

The anionic (meth)acrylate copolymers may be prepared in a manner known per se by free-radical polymerization of the monomers (see, for example, EP 0 704 207 A2 and EP 0 704 208 A2) by radical polymerisation of the monomers in the presence of polymerisation initiators and optionally molecular weight regulators. The copolymers according to the invention are prepared by free-radical emulsion polymerization in aqueous phase in the presence of, preferably, anionic emulsifiers. The process of emulsion polymerization is well known in the art for instance as described in DE-C 2 135 073.

The average molecular weight Mw (weight average, determined for example by measuring the solution viscosity) of the anionic (meth)acrylate copolymers may be for example in the range from 80 000 to 1 000 000 (g/mol).

Process for Preparing an Anionic (Meth)Acrylate Copolymer

An anionic (meth)acrylate copolymer may be produced by radical polymerisation of the monomers in the presence of polymerisation initiators. Molecular weight regulators may be added. The preferred polymerisation method is emulsion polymerisation.

Properties of the Pharmaceutical or Nutraceutical Composition

The pharmaceutical or nutraceutical composition may be characterized in that the release of the pharmaceutical or nutraceutical active ingredient is not more than 10%, preferably is not more than 5% under in-vitro conditions at pH 1.2 for 2 hours in a buffered medium according to USP with and without the addition of 40% (v/v) ethanol.

The Pharmaceutical or nutraceutical composition may be characterized in that the release of the pharmaceutical or nutraceutical active ingredient is not more than 10% under in-vitro conditions at pH 1.2 for 2 hours in a buffered medium according to USP with and without the addition of mM calcium-ions.

The Pharmaceutical or nutraceutical composition may be characterized in that the release of the pharmaceutical or nutraceutical active ingredient is at least 75, preferably 80% under in-vitro conditions at pH 6.8 for 45 min in a buffered medium according to USP.

The Pharmaceutical or nutraceutical composition may be characterized in that the release of the pharmaceutical or nutraceutical active ingredient is at least 75, preferably 80% under in-vitro conditions at pH 5.5 for 45 min in a buffered medium according to USP.

Salts of Alginic Acid

The salts of alginic acid may be selected from sodium alginate, potassium alginate, magnesium alginate, lithium alginate or ammonium alginate or any kind mixtures thereof.

Viscosity

The salts of alginic acid may have a viscosity of 30 to 720, preferably 40 to 450, preferably 40 to 400 or preferably 50 to 300 centipoise (cp) of a 1% aqueous solution (weight/weight).

The methodology of determination of the viscosity of a polymer solution, for instance a solution of a salt of alginic acid, is well known to the skilled person. The viscosity is preferably determined according to European Pharmacopeia $7^{th}$ edition, general chapter 2, methods of analysis, 2.2.8 and 2.2.10, page 27ff. The test is performed using a spindle viscometer.

The viscosity of a 1% alginate solution may be determined by adding 3 g product to 250 ml of distilled water in a beaker while stirring at 800 rpm using overhead stirrer. Then additional 47 ml water was added with rinsing the walls of the beaker. After stirring for 2 hours and getting a complete solution, the viscosity is measured using a LV model of the Brookfield viscometer at 25° C. (77° F.) at 60 rpm with no. 2 spindle for samples with a viscosity of more than 100 cP and at 60 rpm with no. 1 spindle for samples with viscosity less than 100 cP. Since the weight of water is almost exactly 1 g/ml even at 25° C. "weight/weight" is regarded as equal or identical to "weight/volume" in the sense of the invention. Theoretically possible marginal differences are regarded as insignificant.

Addition of Further Polymers to the Gastric Resistant Coating Layer

The pharmaceutical or nutraceutical composition may further comprise, one or more polymers copolymers different from one or more salts of alginic acid and different from one or more polymers or copolymers comprising anionic side groups. For instance one or more water-insoluble polymers or copolymers may be comprised or contained as long as the properties of the pharmaceutical or nutraceutical composition as disclosed herein are not influenced negatively.

The one or more water-insoluble polymers or one or more cellulosic polymers may preferably contain less than 5% by weight, preferably not more than 2% by weight, more preferably not more than 1 or 0.05 to 1% by weight, of monomer residues with anionic side groups.

The one or more water-insoluble polymers or one or more cellulosic polymers may preferably contain less than 12% by weight, preferably not more than 10% by weight, more preferably not more than 5%, of monomer residues with cationic side groups.

Usually the inner coating layer or the outer coating layer may comprise or contain less than 10, less than 5, less than 2, less than 1% by weight of water-insoluble polymers or copolymers calculated either on the content one or more salts of alginic acid in the inner coating layer or respectively on the content of the one or more polymers or copolymers with anionic side groups in the outer coating layer. Usually it is preferred that the inner coating layer or the outer coating layer of the pharmaceutical or nutraceutical composition do not comprise or contain any further polymers or copolymers, most preferably any water-insoluble polymers or copolymers.

Water-Insoluble Polymers

Water-insoluble polymers in the sense of the invention are polymers or copolymers which do not dissolve in water or are only swellable in water over of the whole range of pH 1-14. Water-insoluble polymers may be at the same time polymers containing not more or than 5% of monomer residues with anionic side groups or less than 12 cationic side groups, like for instance EUDRAGIT® NE/NM or EUDRAGIT® RL/RS polymers.

Other kinds of water-insoluble polymers in the sense of the invention may be vinyl copolymers like polyvinylacetate, including derivates of polyvinylacetate. The polyvinylacetate may be present in the form of a dispersion. One example is the type Kollicoat® SR 30 D (BASF), polyvinylacetate dispersion, stabilized with povidone and Na-laurylsulfate.

The water-insoluble polymers may preferably belong to the group of (meth)acrylate copolymers.

EUDRAGIT® NE 30D/EUDRAGIT® NM 30D-Type Polymers

The gastric resistant coating layer may comprise a water-insoluble copolymer which is a copolymer composed of free-radical polymerized units of more than 95% by weight, in particular to an extent of at least 98% by weight, preferably to an extent of at least 99% by weight, in particular to an extent of at least 99% by weight, more preferably to an extent of 100% by weight, of (meth)acrylate monomers with neutral radicals, especially $C_1$- to $C_4$-alkyl radicals. These kinds of polymers do not dissolve in water or are only swellable in water over of the whole range of pH 1-14.

Suitable (meth)acrylate monomers with neutral radicals are, for example, methyl methacrylate, ethyl methacrylate, butyl methacrylate, methyl acrylate, ethyl acrylate, butyl acrylate. Preference is given to methyl methacrylate, ethyl acrylate and methyl acrylate.

Methacrylate monomers with anionic radicals, for example acrylic acid and/or methacrylic acid, may be present in small amounts of less than 5% by weight, preferably not more than 2% by weight, more preferably not more than 1 or 0.05 to 1% by weight.

Suitable examples are neutral or virtually neutral (meth)acrylate copolymers composed of 20 to 40% by weight of ethyl acrylate, 60 to 80% by weight of methyl methacrylate and 0 to less than 5% by weight, preferably 0 to 2 or 0.05 to 1% by weight of methacrylic acid or any methacrylic acid (EUDRAGIT® NE 30D or EUDRAGIT® NM 30D type).

EUDRAGIT® NE 30D and Eudragit® NM 30D are dispersions containing 30% by weight of copolymers composed of free-radically polymerized units of 30% by weight of ethyl acrylate and 70% by weight of methyl methacrylate.

Preference is given to neutral or essentially neutral methyl acrylate copolymers which, according to WO 01/68767, have been prepared as dispersions using 1-10% by weight of a nonionic emulsifier having an HLB value of 15.2 to 17.3. The latter offer the advantage that there is no phase separation with formation of crystal structures by the emulsifier (Eudragit® NM 30D type).

According to EP 1 571 164 A2, corresponding, virtually neutral (meth)acrylate copolymers with small proportions of 0.05 to 1% by weight of monoolefinically unsaturated C3-C8-carboxylic acids can, however, also be prepared by emulsion polymerization in the presence of comparatively small amounts of anionic emulsifiers, for example 0.001 to 1% by weight.

EUDRAGIT® RL/RS-Type Polymers

The gastric resistant coating layer may comprise a water-insoluble copolymer which is a copolymer composed of free-radical polymerized units of 85 to 98% by weight of free-radical polymerized $C_1$ to $C_4$ alkyl esters of acrylic or methacrylic acid and 15 to 2% by weight of (meth)acrylate monomers with a quaternary amino group in the alkyl radical. These kinds of polymers do not dissolve in water or are only swellable in water over of the whole range of pH 1-14.

Cellulosic Polymers

Suitable polymers may also belong to the group of cellulosic polymers, preferably to the group of water soluble celluloses. The cellulosic polymer is preferably a water-soluble cellulose. A suitable cellulosic polymer is hydroxypropylmethyl cellulose (HPMC).

Pharmaceutical or Nutraceutical Active Ingredient

Nutraceuticals

The invention is preferably useful for nutraceutical dosage forms. Nutraceuticals can be defined as extracts of foods claimed to have medical effects on human health. The nutraceutical is usual contained in a medical format such as capsule, tablet or powder in a prescribed dose. Examples for nutraceuticals are resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flavonoids, antioxidants, alpha-linoleic acid from flax seed, beta-carotene from marigold petals or antocyanins from berries. Sometimes the expression neutraceuticals is used as synonym for nutraceuticals.

The gastric resistant pharmaceutical or nutraceutical composition is comprising a core, comprising a pharmaceutical or nutraceutical active ingredient. The pharmaceutical or nutraceutical active ingredient may be a pharmaceutical or nutraceutical active ingredient which may be inactivated under the influence of gastric fluids at pH 1.2 or a pharmaceutical or nutraceutical active ingredient which may irritate the stomach mucosa when set free in the stomach.

Pharmaceutical Active Ingredients

The invention is also preferably useful for enteric coated pharmaceutical dosage forms.

Therapeutical and chemical classes of drugs used in enteric coated pharmaceutical dosage forms are for instance analgetics, antibiotics or anti-infectives, antibodies, antiepileptics, antigens from plants, antirheumatics, betablocker, benzimidazole derivatives, beta-blocker, cardiovascular drugs, chemotherapeutics, CNS drugs, digitalis glycosides, gastrointestinal drugs, e.g. proton pum inhibitors, enzymes, hormons, liquid or solid natural extracts, oligonucleotides, peptidhormon proteins, therapeutical bacteria, peptides, proteins, proton pump inhibitors, (metal)salt f.e. aspartates, chlorides, orthates, urology drugs, vaccines Examples of drugs, which are acid-lablile, irritating or need controlled release, may be: Acamprosat, aescin, amylase, acetylsalicylic acid, adrenalin, 5-amino salicylic acid, aureomycin, bacitracin, balsalazine, beta carotene, bicalutamid bisacodyl, bromelain, bromelain, budesonide, calcitonin, carbamacipine, carboplatin, cephalosporins, cetrorelix, clarithromycin, chloromycetin, cimetidine, cisapride, cladribine, clorazepate, cromalyn, 1-deaminocysteine-8-D-arginine-vasopressin, deramciclane, detirelix, dexlansoprazole, diclofenac, didanosine, digitoxin and other digitalis glycosides, dihydrostreptomycin, dimethicone, divalproex, drospirenone, duloxetine, enzymes, erythromycin, esomeprazole, estrogens, etoposide, famotidine, fluorides, garlic oil, glucagon, granulocyte colony stimulating factor (G-CSF), heparin, hydrocortisone, human growth hormon (hGH), ibuprofen, ilaprazole, insulin, Interferon, Interleukin, Intron A, ketoprofen, lansoprazole, leuprolidacetat lipase, lipoic acid, lithium, kinin, memantine, mesalazine, methenamine, milameline, minerals, minoprazole, naproxen, natamycin, nitrofurantion, novobiocin, olsalazine, omeprazole, orothates, pancreatin, pantoprazole, parathyroidhormone, paroxetine, penicillin, perprazol, pindolol, polymyxin, potassium, pravastatin, prednisone, preglumetacin progabide, pro-somatostatin, protease, quinapril, rabeprazole, ranitidine, ranolazine, reboxetine, rutosid, somatostatin streptomycin, subtilin, sulfasalazine, sulphanilamide, tamsulosin, tenatoprazole, thrypsine, valproic acid, vasopressin, vitamins, zinc, including their salts, derivatives, polymorphs, isomorphs, or any kinds of mixtures or combinations thereof.

Pharmaceutical or Nutraceutical Composition

The pharmaceutical or nutraceutical composition as disclosed herein may be a coated tablet, a coated minitablet, a coated pellet, a coated granule, a sachet, a capsule, filled with coated pellets or with powder or with granules, or a coated capsule, filled with coated pellets or with powder or with granules.

The term coated tablet includes pellet-containing tablets or compressed tablets and is well known to a skilled person. Such a tablet may have a size of around 5 to 25 mm for instance. Usually, defined pluralities of small active ingredient containing pellets are compressed therein together with binding excipients to give the well known tablet form. After oral ingestion and contact with the body fluid the tablet form is disrupted and the pellets are set free. The compressed tablet combines the advantage of the single dose form for ingestion with the advantages of a multiple forms, for instance the dosage accuracy.

The term coated minitablet is well known to the skilled person. A minitablet is smaller than the traditional tablet and may have a size of around 1 to 4 mm. The minitablet is, like a pellet, a single dosage form to be used in multiple dosages. In comparison to pellets, which may be in the same size, minitablets usually have the advantage of having more regular surfaces which can be coated more accurately and more uniformly. Minitablets may be provided enclosed in capsules, such as gelatine capsules. Such capsules disrupt after oral ingestion and contact with the gastric or intestinal fluids and the minitablets are set free. Another application of minitablets is the individual fine adjustment of the active ingredient dosage. In this case the patient may ingest a defined number of minitablets directly which matches to the severe of the decease to cure but also to his individual body weight. A minitablet is different from pellet-containing compressed tablet as discussed above.

The term sachet is well known to the skilled person. It refers to small sealed package which contains the active ingredient often in pellet containing liquid form or also in dry pellet or powder form. The sachet itself is only the package form is not intended to be ingested. The content of the sachet may be dissolved in water or as an advantageous feature may be soaked or ingested directly without further liquid. The latter is advantageous feature for the patient when the dosage form shall be ingested in a situation where no water is available. The sachet is an alternative dosage form to tablets, minitablets or capsules.

Coated pellets may be filled in a capsule, for instance gelatine or HPMC capsule. A capsule containing pellets may also be coated with the enteric coating layer according to the invention.

The gastric resistant pharmaceutical or nutraceutical composition is preferably present in the form of an aqueous coating solution, suspension or dispersion. The dry weight content of the solution, suspension or dispersion may be in the range of 10 to 50, preferably 15 to 35%.

Pharmaceutical or Nutraceutically Acceptable Excipients

The Pharmaceutical or nutraceutical composition may comprise pharmaceutical or nutraceutically acceptable excipients selected from the group of antioxidants, brighteners, binding agents, flavouring agents, flow aids, fragrances, glidants, penetration-promoting agents, pigments, plasticizers, polymers, different from salts of alginic acid and different from the water-insoluble polymers or cellulosic polymers, pore-forming agents or stabilizers or combinations thereof. The pharmaceutical or nutraceutically acceptable excipients may be comprised in the core and/or in the inner coating layer and/or in the outer coating layer.

The inner and/or the outer coating layer comprises up to 60, up to 50, up to 40% by weight of pharmaceutical or nutraceutically acceptable excipients.

Pharmaceutical or nutraceutically acceptable excipients may be selected from the group of antioxidants, brighteners, binding agents, flavouring agents, flow aids, fragrances, glidants, penetration-promoting agents, polymers (different from the salts of alginic acid and different from the polymers or copolymers comprising anionic side groups; excipient polymers can be for instance disintegrants like crosslinked polyvinyl pyrrolidone), pigments, plasticizers, pore-forming agents or stabilizers or combinations thereof.

Process for Producing a Pharmaceutical or Nutraceutical Form

A suitable process for producing the pharmaceutical or nutraceutical composition as disclosed in here may be by forming the core comprising the active ingredient by direct compression, compression of dry, wet or sintered granules, by extrusion and subsequent rounding off, by wet or dry granulation, by direct pelleting or by binding powders onto active ingredient-free beads or neutral cores or active ingredient-containing particles and by applying the inner coating layer and the outer coating layer in the form of aqueous dispersions or organic solutions in spray processes or by fluidized bed spray granulation.

Top Coat and Sub Coats

The pharmaceutical or nutraceutical composition as disclosed herein may be further coated with a sub coat or a top coat or both.

A sub coat may be located between the core and the inner coating layer. A sub coat may have the function to separate substances of the core from substances of the controlling layer which may be incompatible with each other. The sub coat has essentially no influence on the active ingredient release characteristics. A subcoat is preferably essentially water-soluble, for instance it may consist of substances like hydroxypropylmethyl-cellulose (HPMC) as a film former. The average thickness of the subcoat layer is very thin, for example not more than 15 µm, preferably not more than 10 µm.

A top coat may be located on top of the outer coating layer. A top coat is also preferably essentially water soluble. A top coat may have the function of colouring the pharmaceutical or nutraceutical form or protecting from environmental influences for instance from moisture during storage. The top coat may consist out of a binder, for instance a water soluble polymer like a polysaccharide or HPMC, or a sugar compound like saccharose. The top coat may further contain pharmaceutical or nutraceutical excipients like pigments or glidants in high amounts. The topcoat has essentially no influence on the release characteristics.

The expressions sub coat and top coat are well known to the person skilled in the art.

Pellet/Granule/Tablet/Minitablet/Sachet/Capsule

Pharmaceutical or nutraceutical composition may be a coated tablet, a coated minitablet, a coated pellet, a coated granule, a sachet, a capsule, filled with coated pellets or with powder or with granules, or a coated capsule.

Pellets or granules may be used as cores or in compressed tablets. As a rough estimation pellets may have a size in the range of 50 to 1000 µm (average diameter), while coated tablets may have a size in the range of above 1000 µm up to 25 mm (diameter or or length). As a rule one can say the smaller the size of the pellet cores are, the higher the pellet coating weight gain needed. This is due to the comparably higher surface area of pellets compared to tablets.

The term pellet-containing tablet or compressed tablet is well known to a skilled person. Such a tablet may have a size of around 5 to 25 mm for instance. Usually, defined pluralities of small active ingredient containing pellets are compressed therein together with binding excipients to give the well known tablet form. After oral ingestion and contact with the body fluid the tablet form is disrupted and the pellets are set free. The compressed tablet combines the advantage of the single dose form for ingestion with the advantages of a multiple forms, for instance the dosage accuracy. In tablets coatings comparably low amounts of excipients, preferably talcum but also other excipients, may be used in contrast to pellets.

The term minitablet is well known to the skilled person. A minitablet is smaller than the traditional tablet and may have a size of around 1 to 4 mm. The minitablet is, like a pellet, a single dosage form to be used in multiple dosages. In comparison to pellets, which may be in the same size, minitablets usually have the advantage of having more regular surfaces which can be coated more accurately and more uniformly. Minitablets may be provided enclosed in capsules, such as gelatine capsules. Such capsules disrupt after oral ingestion and contact with the gastric or intestinal fluids and the minitablets are set free. Another application of minitablets is the individual fine adjustment of the active ingredient dosage. In this case the patient may ingest a defined number of minitablets directly which matches to the severe of the decease to cure but also to his individual body weight. A minitablet is different from pellet-containing compressed tablet as discussed above.

The term sachet is well known to the skilled person. It refers to small sealed package which contains the active ingredient often in pellet containing liquid form or also in dry pellet or powder form. The sachet itself is only the package form is not intended to be ingested. The content of the sachet may be dissolved in water or as an advantageous feature may be soaked or ingested directly without further liquid. The latter is advantageous feature for the patient when the dosage form shall be ingested in a situation where no water is available. The sachet is an alternative dosage form to tablets, minitablets or capsules.

The term capsule is well known to the skilled person. A capsule is like the sachet a container for pellets containing liquids or also dry pellets or powders. However in contrast to the sachet the capsule consists of pharmaceutically acceptable excipients such as gelatine or hydroxypropylmethylcellulose and is intended to be ingested like a tablet.

The capsules disrupts after oral ingestion and contact with the gastric or intestinal fluids and the contained multiple units are set free. Capsules for pharmaceutical purposes are commercially available in different standardized sizes.

Use

The pharmaceutical or nutraceutical composition as described herein may be used as a gastric resistant pharmaceutical or nutraceutical composition with resistance against the influence of ethanol and with resistance against the influence of calcium ions.

EXAMPLES

Abbreviations

L30D-55=EUDRAGIT® L30D-55
L100-55=EUDRAGIT® L100-55
FS30D=EUDRAGIT® FS30D
NM30D=EUDRAGIT® NM30D
Calculations:
Amount Polymer Coating [%]: % by weight calculated on the weight of the core
Ratio Outer/Inner Coating: % by weight polymer outer coating divided by % by weight polymer inner coating multiplied with 100. Equal levels give 100.
Other excipients: % by weight calculated on the weight of the polymer Preparation of Core Caffeine Pellets Drug Layering
Core used: Non pareil seeds (size 707-841 microns)
Quantity taken: 600.0 gm
Formula:

| Ingredients | Manufacturer | Solid content (g) | Qty. batch (g) |
|---|---|---|---|
| Caffeine anhydrous | Aarti Drugs | 600 | 600 |
| Hydroxypropyl methyl cellulose (Pharmacoat 603) | Shin-Etsu | 85.5 | 85.5 |
| Yellow iron oxide | BASF | 3 | 3 |
| Water | | | 7917.75 |
| Total | | 688.5 | 8606.25 |

Total solid content: 8% w/w
Procedure for Drug Layering Suspension Preparation:
1. Caffeine was passed through sieve of 149 micron (100#)
2. Hydroxypropyl methyl cellulose was accurately weighed and dissolved in 7000 g water using an overhead stirrer.
3. Caffeine of step 1 was added to solution of step 2 under homogenization.
4. Homogenisation of step 2 was continued for 60 minutes.
5. Washing was given to the homogeniser with the remaining water and added to the final suspension.
6. The final prepared suspension was passed through a sieve of 420 microns (40#).
7. This suspension was further sprayed onto pellets in fluid bed processor.
8. After completion of spraying pellets were dried in fluid bed processor till the LOD was less than 2% w/w Equipment and in Process Coating Parameters:
Machine parameters: GPCG 3.1
Column height: 20-30 mm
Nozzle bore: 0.8 mm
Air flow mode: Auto
Inlet temp: 62-66° C.
Product temp: 38-43° C.
Atomisation Pressure: 1.0-1.1 bar
Spray rate: 17-31 gm/min
Silicon tube ID: 5 mm
Filter shaking mode: Asynchronous
Filter shaking: 5 sec
Filter shaking pause: 50 sec
Air flow: 130-142 m$^3$/h
Release Rate of the Uncoated Pellets:
96% drug release obtained after 10 minutes in pH 6.8 buffer Metoprolol Succinate Pellets Drug Layering
Core used: Non pareil seeds (size 707-84 1 microns)
Quantity taken: 600.0 gm
Formula:

| Ingredients | Manufacturer | Solid content (g) | Qty. batch (g) |
|---|---|---|---|
| Metoprolol succinate | Polydrug lab Pvt Ltd | 600 | 600 |
| Polyvinylpyrrolidone (Kollidon 30) | BASF | 120 | 120 |
| Yellow iron oxide | BASF | 4.2 | 4.2 |
| Water | | | 1679 |
| Total | | 724.2 | 2403.2 |

Total solid content: 30.13% w/w
Procedure for Drug Layering Suspension Preparation:
1. Polyvinylpyrrolidone was accurately weighed and dissolved in 1200 g water using an overhead stirrer.
2. Aerosil was added to solution of step 2 under stirring
3. Metoprolol succinate was added to suspension of step 1 and stirring was continued for 30 minutes.
4. The final prepared suspension was passed through a sieve of 250 microns (60#).
5. This suspension was further sprayed onto pellets in fluid bed processor.
6. After completion of spraying pellets were dried in fluid bed processor till the LOD was less than 2% w/w Equipment and in Process Coating Parameters:
Machine parameters: GPCG 3.1
Column height: 20 mm
Nozzle bore: 0.8 mm
Air flow mode: Auto
Inlet temp: 60-63° C.
Product temp: 44-52° C.
Atomisation Pressure: 1-1.1 bar
Spray rate: 5-9.7 gm/min
Silicon tube ID: 5 mm
Filter shaking mode: Asynchron
Filter shaking: 5 sec
Filter shaking pause: 150 sec
Air flow: 128-135 m$^3$/h
Release Rate of the Uncoated Pellets:
94% drug release obtained after 10 minutes in pH 6.8 buffer Lansoprazole Pellets 1. Drug layering
2. Barrier coating Drug Layering
Core used: Non pareil seeds (size 600-710 microns)
Quantity taken: 600.0 gm
Formula:

| Ingredients | Manufacturer | Solid content (g) | Qty. batch (g) |
|---|---|---|---|
| Lansoprazole | Metrochem API Pvt. Ltd. | 450 | 450 |
| Sucrose | M.B Sugars and Pharmaceuticals Ltd. | 750 | 750 |
| Hydroxypropyl methyl cellulose (Pharmacoat 606) | Shin-Etsu | 105 | 105 |
| L -HPC LH 21 | Shin-Etsu | 195 | 195 |
| Water | | | 3500 |
| Total | | 1500 | 5000 |

Total solid content: 30% w/w
Procedure for Drug Layering Suspension Preparation:
1. L-HPC LH 21 was accurately weighed and suspended in 200 g water using an overhead stirrer and stirring was continued for 20 minutes.
2. Hydroxypropyl methyl cellulose was dissolved in 1000 g water with stirring and stirring was continued for 20 minutes and then added to suspension of step 1
3. Lansoprazole and sucrose was mixed in a polybag for 5 minutes and then added to suspension of step 1
4. The remaining water was added to step 1 and stirring was continued for 20 minutes.
5. The final prepared suspension was passed through a sieve of 420 microns (40#).
6. This suspension was further sprayed onto pellets in fluid bed processor.
7. After completion of spraying pellets were dried in fluid bed processor till the LOD was less than 2% w/w Equipment and in Process Coating Parameters:
Machine parameters: GPCG 3.1
Column height: 16-25 mm
Nozzle bore: 0.8 mm
Air flow mode: Auto
Inlet temp: 52-61° C.
Product temp: 35-44° C.
Atomisation Pressure: 1.0-1.3 bar
Spray rate: 3.5-24.8 gm/min
Silicon tube ID: 4 mm
Filter shaking mode: Asynchronous
Filter shaking: 5 sec
Filter shaking pause: 200 sec
Air flow: 75-135 m³/h
Release Rate of the Uncoated Pellets:
97% drug release obtained after 10 minutes in pH 6.8 buffer
Barrier Coating
Core used: Drug layered lansoprazole pellets
Quantity taken: 800.0 gm
Formula: 20% coating on 800 g pellets

| Ingredients | Manufacturer | Solid content (g) | Qty. batch (g) |
|---|---|---|---|
| Hydroxypropyl methyl cellulose (Pharmacoat 606) | Shin-Etsu | 160 | 160 |
| Light magnesium carbonate | SCORA.S.A | 320 | 320 |
| Talc | Luzenac | 32 | 32 |
| Water | | | 2901.33 |
| Total | | 512 | 3413.33 |

Total solid content: 15% w/w
Procedure for Drug Layering Suspension Preparation:
1. Hydroxypropyl methyl cellulose was dissolved in 1400 g water with stirring using an overhead stirrer and stirring was continued for 30 minutes
2. Talc and Light magnesium carbonate were homogenized in 1400 g for 30 minutes and added to solution of step 1
3. The remaining water was added to step 1 and stirring was continued for 20 minutes.
4. The final prepared suspension was passed through a sieve of 420 microns (40#).
5. This suspension was further sprayed onto pellets in fluid bed processor.
6. After completion of spraying pellets were dried in fluid bed processor till the LOD was less than 2% w/w Equipment and in Process Coating Parameters:
Machine parameters: GPCG 3.1
Column height: 17-23 mm
Nozzle bore: 1.2 mm
Air flow mode: Auto
Inlet temp: 58-65° C.
Product temp: 41-44° C.
Atomisation Pressure: 1.0-1.3 bar
Spray rate: 3-17 gm/min
Silicon tube ID: 4 mm
Filter shaking mode: Asynchronous
Filter shaking: 5 sec
Filter shaking pause: 300 sec
Air flow: 110-135 m³/h
Results:
96% drug release obtained after 10 minutes in pH 6.8 buffer Reparation of Core Duloxetine Hydrochloride Pellets Drug Layering
Core used: Non pareil seeds (size 707-841 microns)
Quantity taken: 350 gm
Formula:

| Ingredients | Manufacturer | Solid content (g) | Qty. batch (g) |
|---|---|---|---|
| Duloxetine HCl | Aurbindo Pharma | 200 | 200 |
| Polyplasdone ® XL-10 | ISP | 117 | 117 |
| Hydroxypropyl methyl cellulose (Pharmacoat 603) | Shin-Etsu | 24 | 24 |
| Water | | | 1276 |
| Total | | 341 | 1617 |

Total solid content: 21.08% w/w

Procedure for Drug Layering Suspension Preparation:
1. Hydroxypropyl methyl cellulose was dissolved in 795 g water using an overhead stirrer.
2. Polyplasdone XL-10 was added to solution of step 1 under stirring and stirring was continued for 15 minutes.
3. Duloxetine HCl was accurately weighed and added to suspension of step I under stirring and stirring was continued for 15 minutes.
4. The final prepared suspension was passed through a sieve of 420 microns (40#).
5. This suspension was further sprayed onto pellets in fluid bed processor.
6. After completion of spraying pellets were dried in fluid bed processor till the LOD was less than 2% w/w Equipment and in Process Coating Parameters:
Machine parameters: GPCG 1.1
Column height: 20-30 mm
Nozzle bore: 0.8 mm
Air flow mode: Auto
Inlet temp: 44-49° C.
Product temp: 29-38° C.
Atomisation Pressure: 1 bar
Spray rate: 5-16 g/min
Silicon tube ID: 5 mm
Filter shaking mode: Asynchron
Filter shaking: 5 sec
Filter shaking pause: 50 sec
Air flow: 52-64 CFM Release Rate of the Uncoated Pellets:
89% drug release obtained after 30 minutes in pH 6.8 buffer Caffeine Mini-Tablets Formula: 200,000 tablets
Granulation:Formula for 200000 tablets

| Ingredient | Manufacturer | mg/tab | Quatity required for 200000 tablets |
|---|---|---|---|
| Caffeine | Aarti Drugs Ltd. | 3.50 | 700 |
| Avicel 101 | FMC Biopolymer | 1.50 | 300 |
| Polyvinylpyrrolidone (Kollidon 30) | BASF | 1.50 | 300 |
| Sodium Starch glycolate | Roquette Extragranular | 0.12 | 24 |
| Avicel 200 | FMC Biopolymer | 0.25 | 50 |
| Aerosil | | 0.06 | 12 |
| Talc | Luznac | 0.07 | 14 |
| Magnesium stearate | Ferro Corporation | 0.03 | 6 |
| Total | | 7.03 | 1406 |

Granulation Procedure:
1. Caffeine was passed through 420 microns (40#) sieve and accurately weighed.
2. PVP K 30 solution was made by dissolving the weighed quantity in 480 gm water using an overhead stirrer.
3. SSG and Avicel 101 was weighed and mixed with caffeine in planetary mixer for 10 minutes.
4. The blend of step 3 was granulated with PVP K30 solution using a planetary mixer.
5. Granules obtained were passed through 1680 microns (12#) sieve and taken for drying.

Compression Procedure:
1. Avicel 200, SSG and Aerosil were passed through 420 microns (40#) sieve and weighed accurately.
2. Granules were passed through 595 microns (30#) sieve and weighed accurately and mixed with Avicel 200, SSG & Aerosil in a polybag for 5 minutes.
3. Magnesium Stearate was passed through 250 microns (60#) sieve and weighed accurately.
4. Talc and Magnesium Stearate were added to the blend of step 2 and mixed in polybag for 1 min.
5. The blend was compressed on a 16 station rotary compression machine using 2 mm circular standard concave punches Tablet Parameters:

| Sr. No. | Tests | Values |
|---|---|---|
| 1. | Weight of tablet (in mg) | 6-8 |
| 2. | Hardness | 30-40 Kg/cm$^2$ |
| 3. | Friability(at 500 rpm) | Nil |
| 4. | Thickness of tablets | 1.4-1.7 mm |
| 5. | Disintegration time | 1-2 minutes |

Release Rate of the Uncoated Mini-Tablets:
89% drug release obtained after 10 minutes in pH 6.8 buffer Preparation of Caffeine Tablets Formula for 5000 Tablets

| Ingredient | Manufacturer | mg/tab | Qty required for 5000 Tablets (g) |
|---|---|---|---|
| Caffeine | Aarti Drugs Ltd. | 200 | 1000 |
| Avicel 101 | FMC Biopolymer | 84 | 420 |
| Avicel 200 | FMC Biopolymer | 84 | 420 |
| PVPK 30 | BASF | 14 | 70 |
| Sodium Starch glycolate | Roquette | 8 | 40 |
| Aerosil | Evonik Industries | 4 | 20 |
| Talc | Luznac | 6 | 30 |
| Magnesium stearate | Ferro Corporation | 2 | 10 |
| | | 402 | 2010 |

Procedure for Tablet Preparation:
1. All ingredients were sifted through 40 mesh sieve (425 microns) and weighed accurately.
2. Caffeine, Avicel® 101, Avicel®200, sodium starch glycolate and PVP K 30 were mixed in cone blender for 3 minutes
3. Talc and aerosol were sifted together through 60 mesh sieve (250 microns) and blended with blend of step 2 in a cone blender for 2 minutes.
4. Aerosil was added to the blend of step 2 and mixed for 2 minutes in cone blender
5. The loss on drying for the blend was checked on a moisture balance. (If LOD was more than 2% w/w then blend was dried in a tray dryer at 40° C. till the LOD was below 2% w/w)
6. Magnesium stearate was sifted through 80 mesh sieve (177 microns) and blended with the blend of step 2 was lubricated with Magnesium stearate in a cone blender for 2 minutes.

7. The blend was compressed on a 16 station rotary compression machine using 11 mm circular standard concave punches Tablet Parameters:

| Sr. No. | Tests | Values |
|---|---|---|
| 1. | Weight of tablet (in mg) | 400 ± 5% |
| 2. | Hardness | 7-9 Kg/cm$^2$ |
| 3. | Friability(at 500 rpm) | <1% |
| 4. | Thickness of tablets | 4.69 ± 0.1 mm |
| 5. | Disintegration time | <1 minute |

Results:

81% drug release obtained after 10 minutes in pH 6.8 buffer

Coating Process

Alginic Acid and Salts Used in Examples

| Commercial Name | Supplier | Viscosity Specification | Calculated Viscosity for 1% solution comparative |
|---|---|---|---|
| Sodium alginate | | | |
| KELTONE ® LVCR | FMC Biopolymers | 100-300 cP for 2% w/w solution | 50-150 cP for 1% w/w solution |
| Potassium alginate | | | |
| PROTANAL ® KF 200 FTS | FMC Biopolymers | 200-400 cP for 1% w/w solution | 200-400 cP for 1% w/w solution |
| Amonium a ginate | | | |
| ALGIN ® NH-LV | KIMICA CORPORATION | 250-550 cP at 1% w/w solution | 250-550 cP for 1% w/w solution |

Analytical Methodology

1. Caffeine Pellets

A) Dissolution Conditions

1) Dissolution Parameters

Apparatus: USP Type II

Dissolution Medium: Acid stage medium for 2 hrs followed by buffer stage medium (1 hr)

Volume of Medium: 750 mL for acid stage, 1000 mL for buffer stage

Speed: 50 rpm

Temperature: 37° C.±0.5° C.

Withdrawal Volume: 10 ml

Sampling point: Acid stage—2 hour, Buffer stage—45 minutes

2) Dissolution Mediums

I. Acid stage medium—0.1 N HCl; Buffer stage medium—pH 6.8 PO4 buffer

II. Acid stage medium—0.1 N HCl; Buffer stage medium—pH 5.5 Acetate buffer

III. Acid stage medium—Alcoholic 0.1 N HCl (5%, 10%, 20%, 40%); Buffer stage medium—pH 6.8 PO4 buffer IV. Acid stage medium—0.1 N HCl with Ca; Buffer stage medium—pH 6.8 PO4 buffer with Ca V. Acid stage medium—0.1 N HCl with Ca; Buffer stage medium—pH 6.8 PO4 buffer 3) Composition of Dissolution Mediums 1) Buffer pH 6.8—

19.01 g of Trisodium Phosphate was weighed and transferred to 1 liter beaker. To this, 500 mL water and 6.37 mL of conc. hydrochloric acid was added and volume was made up to 1000 mL with water. The pH was adjusted to 6.8±0.05 using 2N NaOH or 2N HCl.

2) Buffer pH 5.5—

5.99 g of Sodium acetate trihydrate was weighed and transferred to 1 liter beaker. To this water was added and volume was made up to 1000 mL with water. The pH was adjusted to 5.5±0.05 using glacial acetic acid.

3) Buffers with Calcium—

0.185 g of Calcium chloride di-hydrate was weighed and mixed with 1 liter buffer solutions.

4) Dissolution Procedure:

Acid Stage: Accurately weighed pellets of caffeine were transferred in six different dissolution jars and then the dissolution test was performed as per parameters given in the method above (Acid Stage). After 2 hr 10 mL of aliquot was removed and analysed as acid stage sample solution.

Buffer Stage: The pellets after acid stage were transferred to buffer stage medium pH 6.8. The dissolution test was continued as per parameters given in the method above (Buffer Stage). The aliquots of each interval ware filtered through 0.45 μm nylon membrane syringe filter discarding first few mL of the filtrate and analysed as buffer stage sample solution.

B) Chromatographic Conditions

Column: Agilent Zorbax Eclipse XDB C8 column, 150×4.6 mm, 5 μm or equivalent

Mobile Phase: Water: Acetonitrile: (80:20)

Wavelength: 273 nm

Column Temp: 25° C.

Injection Volume: 10 μL

Flow rate: 1 mL/minute

Run time: 5 minutes

C) Acceptance Criteria

Acid stage: Less than 10% drug release after 2 hours

Buffer stage: More than 75% drug release within 45 minutes in buffer 6.8

2. Caffeine Minitablets

A) Dissolution Conditions

1) Dissolution Parameters

Apparatus: USP Type I

Dissolution Medium: Acid stage medium for 2 hrs followed by buffer stage medium (1 hr)

Volume of Medium: 750 mL for acid stage, 1000 mL for buffer stage

Speed: 100 rpm

Temperature: 37° C.±0.5° C.

Withdrawal Volume: 10 ml

Sampling point: Acid stage—2 hour, Buffer stage—45 minutes

2) Dissolution Mediums
As mentioned in Caffeine pellets.
3) Composition of Dissolution Mediums
As mentioned in Caffeine pellets.
4) Dissolution Procedure:
Acid Stage: Accurately weighed minitablets of caffeine were transferred in six different dissolution jars and then the dissolution test was performed as per parameters given in the method above (Acid Stage). After 2 hr 10 mL of aliquot was removed and analysed as acid stage sample solution.
Buffer Stage: The minitablets after acid stage were transferred to buffer stage medium pH 6.8. The dissolution test was continued as per parameters given in the method above (Buffer Stage). The aliquots of each interval ware filtered through 0.45 µm nylon membrane syringe filter discarding first few mL of the filtrate and analysed as buffer stage sample solution.
B) Chromatographic Conditions
As mentioned in Caffeine pellets.
C) Acceptance Criteria
  Acid stage: Less than 10% drug release after 2 hours
  Buffer stage: More than 75% drug release within 45 minutes in buffer 6.8
3. Caffeine Capsules
A) Dissolution Conditions
1) Dissolution Parameters
Apparatus: USP Type I
Dissolution Medium: Acid stage medium for 2 hrs followed by buffer stage medium (1 hr)
Volume of Medium: 750 mL for acid stage, 1000 mL for buffer stage
Speed: 100 rpm
Temperature: 37° C.±0.5° C.
Withdrawal Volume: 10 ml
Sampling point: Acid stage—2 hour, Buffer stage—45 minutes
2) Dissolution Mediums
As mentioned in Caffeine pellets.
3) Composition of Dissolution Mediums
As mentioned in Caffeine pellets.
4) Dissolution Procedure:
Acid Stage: Accurately weighed capsules of caffeine were transferred in six different dissolution jars and then the dissolution test was performed as per parameters given in the method above (Acid Stage). After 2 hr 10 mL of aliquot was removed and analysed as acid stage sample solution.
Buffer Stage: The capsules after acid stage were transferred to buffer stage medium pH 6.8. The dissolution test was continued as per parameters given in the method above (Buffer Stage). The aliquots of each interval ware filtered through 0.45 µm nylon membrane syringe filter discarding first few mL of the filtrate and analysed as buffer stage sample solution.
B) Chromatographic Conditions
As mentioned in Caffeine pellets.
C) Acceptance Criteria
  Acid stage: Less than 10% drug release after 2 hours
  Buffer stage: More than 75% drug release within 45 minutes in buffer 6.8
4. Caffeine Tablets
A) Dissolution Conditions
1) Dissolution Parameters
Apparatus: USP Type II
Dissolution Medium: Acid stage medium for 2 hrs followed by buffer stage medium (1 hr)
Volume of Medium: 750 mL for acid stage, 1000 mL for buffer stage
Speed: 50 rpm
Temperature: 37° C.±0.5° C.
Withdrawal Volume: 10 ml
Sampling point: Acid stage—2 hour, Buffer stage—45 minutes
2) Dissolution Mediums
As mentioned in Caffeine pellets.
3) Composition of Dissolution Mediums
As mentioned in Caffeine pellets.
4) Dissolution Procedure:
Acid Stage: Accurately weighed tablets of caffeine were transferred in six different dissolution jars and then the dissolution test was performed as per parameters given in the method above (Acid Stage). After 2 hr 10 mL of aliquot was removed and analysed as acid stage sample solution.
Buffer Stage: The tablets after acid stage were transferred to buffer stage medium pH 6.8. The dissolution test was continued as per parameters given in the method above (Buffer Stage). The aliquots of each interval ware filtered through 0.45 µm nylon membrane syringe filter discarding first few mL of the filtrate and analysed as buffer stage sample solution.
B) Chromatographic Conditions
As mentioned in Caffeine pellets.
C) Acceptance Criteria
  Acid stage: Less than 10% drug release after 2 hours
  Buffer stage: More than 75% drug release within 45 minutes in buffer 6.8
5. Lansoprazole pellets
A) Dissolution Conditions
1) Dissolution Parameters
a) Acid Stage
Apparatus: USP Type II
Dissolution Medium: 0.1N HCl
Volume of Medium: 500 ml
Speed: 75 rpm
Temperature: 37° C.±0.5° C.
Withdrawal Volume: 25 ml
Time: 60 minutes
Detection Wavelength: 306 nm
b) Buffer Stage
Apparatus: USP Type II
Dissolution Medium: Buffer stage medium pH 6.8 (Refer note below)
Volume of Medium: 900 ml
Speed: 75 rpm
Temperature: 37° C.±0.5° C.
Withdrawal Volume: 10 ml
Time Points: 60 minutes
Detection Wavelength: Difference between absorbance at 286 nm and 650 nm
Buffer Stage Medium:
Buffer stage medium is a mixture of acid stage medium (475 mL) and phosphate buffer concentrate (425 mL) with pH adjusted to 6.8.
2) Dissolution Mediums
I. Acid stage medium—0.1 N HCl; Buffer stage medium—pH 6.8 buffer
II. Acid stage medium—0.1 N HCl; Buffer stage medium—pH 5.5 buffer
III. Acid stage medium—Alcoholic 0.1 N HCl (5%, 10%, 20%, 40%)

3) Composition of Dissolution Mediums
1) Preparation of Phosphate Buffer Concentrate—
Accurately weighed 16.3 g of monobasic sodium Phosphate, 7.05 g of sodium hydroxide, 3.0 g of Sodium dodecyl sulfate and was dissolved in water and volume was made up till one liter and mixed well.
2) Buffer pH 6.8—
Buffer stage medium was prepared by mixing 475 mL of 0.1N HCl and 425 mL of phosphate buffer concentrate, the pH was adjusted to 6.8.
3) Buffer pH 5.5—
Buffer stage medium was prepared by mixing 475 mL of 0.1N HCl and 425 mL of phosphate buffer concentrate, the pH was adjusted to 5.5 with orthophosphoric acid.
4) Dissolution Procedure:
Acid Stage: Transferred accurately weighed pellets of lansoprazole (equivalent to 30 mg) in six different dissolution jars and then the dissolution test was performed as per parameters given in the method above (Acid Stage). After 1 hour 25 mL of aliquot was removed and analysed as acid stage sample solution.
Buffer Stage: 425 mL of Phosphate buffer concentrate was added to the acid stage medium (Buffer Stage This will provide total of 900 mL pH 6.8 medium). The dissolution test was continued as per parameters given in the method above. The aliquots of each interval were filtered through 0.45 μm nylon membrane syringe filter discarding first few mL of the filtrate and analysed as buffer stage sample solution.
In case of dissolution with Buffer pH 5.5, the pellets were transferred after acid stage to 900 mL of buffer solution pH 5.5.
C) Acceptance Criteria
Acid stage: Less than 10% drug release after 1 hour
Buffer stage: More than 75% drug release within 45 minutes in buffer 6.8

6. Duloxetine Pellets
A) Dissolution Conditions
1) Dissolution Parameters
Apparatus: USP Type I
Dissolution Medium: Acid stage medium for 2 hrs followed by buffer stage medium (1 hr)
Volume of Medium: 1000 mL for acid stage, 1000 mL for buffer stage
Speed: 100 rpm
Temperature: 37° C.±0.5° C.
Withdrawal Volume: 10 ml
Sampling point: Acid stage—2 hour, Buffer stage—90 minutes
2) Dissolution Mediums
I. Acid stage medium—0.1 N HCl; Buffer stage medium—pH 6.8 PO4 buffer
II. Acid stage medium—0.1 N HCl; Buffer stage medium—pH 5.5 Acetate buffer
III. Acid stage medium—Alcoholic 0.1 N HCl (5%, 10%, 20%, 40%)
3) Composition of Dissolution Mediums
1) Buffer pH 6.8—
19.01 g of Trisodium Phosphate was weighed and transferred to 1 liter beaker. To this, 500 mL water and 6.37 mL of conc. hydrochloric acid was added and volume was made up to 1000 mL with water. The pH was adjusted to 6.8±0.05 using 2N NaOH or 2N HCl.
2) Buffer pH 5.5—
5.99 g of Sodium acetate trihydrate was weighed and transferred to 1 liter beaker. To this water was added and volume was made up to 1000 mL with water. The pH was adjusted to 5.5±0.05 using glacial acetic acid.
4) Dissolution Procedure:
Acid Stage: Accurately weighed pellets of duloxetine were transferred in six different dissolution jars and then the dissolution test was performed as per parameters given in the method above (Acid Stage). After 2 hr 10 mL of aliquot was removed and analysed as acid stage sample solution.
Buffer Stage: The pellets after acid stage were transferred to buffer stage medium pH 6.8. The dissolution test was continued as per parameters given in the method above (Buffer Stage). The aliquots of each interval ware filtered through 0.45 μm nylon membrane syringe filter discarding first few mL of the filtrate and analysed as buffer stage sample solution.
B) Chromatographic Conditions
Column: Agilent Zorbax Eclipse XDB C8 column, 150×4.6 mm, 5 μm or equivalent
Mobile Phase: Buffer: Acetonitrile: (60:40)
Wavelength: 230 nm
Column Temp: 25° C.
Injection Volume: 10 μL
Flow rate: 1 mL/minute
Preparation of Buffer for Mobile Phase:
1.36 gram of potassium dihydrogen phosphate was dissolved in 1000 ml of water and was filtered through 0.45 μm nylon membrane filter.
C) Acceptance Criteria
Acid stage: Less than 10% drug release after 2 hours
Buffer stage: More than 60% drug release within 90 minutes in buffer 6.8

7. Metoprolol Succinate Pellets
A) Dissolution Conditions
1) Dissolution Parameters
Apparatus: USP Type II
Dissolution Medium: Acid stage medium for 2 hrs followed by buffer stage medium (1 hr)
Volume of Medium: 750 mL for acid stage, 1000 mL for buffer stage
Speed: 50 rpm
Temperature: 37° C.±0.5° C.
Withdrawal Volume: 10 ml
Sampling point: Acid stage—2 hour, Buffer stage—45 minutes
2) Dissolution Mediums
VI. Acid stage medium—0.1 N HCl; Buffer stage medium—pH 6.8 PO4 buffer
VII. Acid stage medium—0.1 N HCl; Buffer stage medium—pH 5.5 Acetate buffer
VIII. Acid stage medium—ethanolic 0.1 N HCl (5%, 10%, 20%, 40%); Buffer stage medium—pH 6.8 PO4 buffer
IX. Acid stage medium—0.1 N HCl with Ca; Buffer stage medium—pH 6.8 PO4 buffer with Ca
X. Acid stage medium—0.1 N HCl with Ca; Buffer stage medium—pH 6.8 PO4 buffer
3) Composition of Dissolution Mediums
1) Buffer pH 6.8—
19.01 g of Trisodium Phosphate was weighed and transferred to 1 liter beaker. To this, 500 mL water and 6.37 mL of conc. hydrochloric acid was added and volume was made up to 1000 mL with water. The pH was adjusted to 6.8±0.05 using 2N NaOH or 2N HCl.
2) Buffer pH 5.5—
5.99 g of Sodium acetate trihydrate was weighed and transferred to 1 liter beaker. To this water was added and volume was made up to 1000 mL with water. The pH was adjusted to 5.5±0.05 using glacial acetic acid.

3) Buffers with Calcium—

0.185 g of Calcium chloride di-hydrate was weighed and mixed with 1 liter buffer solutions.

4) Dissolution Procedure:

Acid Stage: Accurately weighed pellets of metoprolol succinate were transferred in six different dissolution jars and then the dissolution test was performed as per parameters given in the method above (Acid Stage). After 2 hr 10 mL of aliquot was removed and analysed as acid stage sample solution.

Buffer Stage: The pellets after acid stage were transferred to buffer stage medium pH 6.8. The dissolution test was continued as per parameters given in the method above (Buffer Stage). The aliquots of each interval ware filtered through 0.45 μm nylon membrane syringe filter discarding first few mL of the filtrate and analysed as buffer stage sample solution.

B) Chromatographic Conditions

Column: Agilent Zorbax Eclipse XDB C8 column, 150×4.6 mm, 5 μm or equivalent

Mobile Phase: Buffer: Acetonitrile: (75:25)

Wavelength: 280 nm

Column Temp: 30° C.

Injection Volume: 20 μL

Flow rate: 1 mL/minute

Preparation of Buffer for Mobile Phase:

9.0 gram of Sodium dihydrogen Phosphate was dissolved in 1000 ml of water, the pH of the solution was adjusted to 3.0 with orthophosphoric acid. The buffer was filtered through 0.45 μm nylon membrane filter.

C) Acceptance Criteria

Acid stage: Less than 10% drug release after 2 hours
Buffer stage: More than 75% drug release within 45 minutes in buffer 6.8

Caffeine Pellets

Example 1C (Comparative)

Potassium Alginate (200-400 cP for 1% w/w Solution) with Aerosil (10% w.r.t Potassium Alginate)

Coating of 30% potassium alginate
Formula for 30% w/w Polymer Coating on 600 g Pellets

| Ingredient | Manufacturer | Quantity/Batch [g] | Solid content [g] |
| --- | --- | --- | --- |
| Potassium alginate | FMC Biopolymers | 180 | 180 |
| Talc | Luzenac | 270 | 270 |
| Aerosil ® | Evonik Industries | 18 | 18 |
| Purified Water | | 11232 | |
| Total | | 11700 | 468 |

Solid Content of Coating Suspension: 4% w/w
Procedure for Coating Suspension Preparation:
1. Potassium Alginate was weighed and kept under stirring with water for 60 minutes on an overhead stirrer to prepare 2% solution.
2. Talc and Aerosil were homogenized with remaining amount of water for 30 minutes.
3. Homogenized talc suspension was added to Alginate solution and stirring was continued for further 30 mins.
4. The final prepared suspension was passed through a sieve of 420 microns (40#).
5. This suspension was further sprayed onto pellets in fluid bed processor.

Equipment and in Process Coating Parameters for Pellets:
Instrument used: GPCG 3.1
Silicone tube: 5.0 mm inner diameter
Column height: 10-30 mm
Nozzle bore: 0.8 mm
Filter shaking mode: Asynchronous
Filter shaking: 10 sec
Filter shaking pause: 100 sec
Air flow mode: Auto
Air flow: 120-180 m$^3$/h
Atomisation pressure: 1.0-1.5 bar
Inlet temperature: 46-72° C.
Product temperature: 32° C.-49° C.
Spray rate: 5-17 g/min
Observation:
Agglomeration of pellets was observed in pH 6.8 buffer.

Example 2C (comparative)

Potassium Alginate (200-400 cP for 1% w/w Solution) with Sipernate 160 PQ (15% w.r.t Potassium Alginate)

Coating of 30% potassium alginate
Formula for 30% w/w Polymer Coating on 600 g Pellets

| Ingredient | Manufacturer | Quantity/Batch [g] | Solid content [g] |
| --- | --- | --- | --- |
| Potassium alginate | FMC Biopolymers | 180 | 180 |
| Talc | Luzenac | 360 | 360 |
| Sipernate 160PQ | Evonik Industries | 27 | 27 |
| Purified Water | | 13608 | |
| Total | | 14175 | 567 |

Solid Content of Coating Suspension: 4% w/w
Procedure for Coating Suspension Preparation:
1. Potassium Alginate was weighed and kept under stirring with water for 60 minutes on an overhead stirrer to prepare 2% solution.
2. Sipernate 160PQ was dispersed in 500 μm water using overhead stirrer and then added to potassium alginate solution.
3. Talc was homogenized with remaining amount of water for 30 minutes.
4. Homogenized talc suspension was added to potassium Alginate solution and stirring was continued for further 30 mins.
5. The final prepared suspension was passed through a sieve of 420 microns (40#).
6. This suspension was further sprayed onto pellets in fluid bed processor.

Equipment and in Process Coating Parameters for Pellets:
Instrument used: GPCG 3.1
Silicone tube: 5.0 mm inner diameter
Column height: 10-25 mm
Nozzle bore: 0.8 mm
Filter shaking mode: Asynchronous
Filter shaking: 10 sec
Filter shaking pause: 100 sec Air flow mode: Auto
Air flow: 160-175 m³/h
Atomisation pressure: 1.3 bar
Inlet temperature: 65-68° C.
Product temperature: 41° C.-45° C.
Spray rate: 18-21 g/min
Observation:
  Agglomeration of pellets was observed in pH 6.8 buffer.

Example 3C (Comparative)

Potassium Alginate (200-400 cP for 1% w/w Solution) with Hydroxypropyl methyl Cellulose (10% w.r.t Potassium Alginate)

Coating of 15% potassium alginate
Formula for 15% w/w Polymer Coating on 600 g Pellets

| Ingredient | Manufacturer | Quantity/Batch [g] | Solid content [g] |
|---|---|---|---|
| Potassium alginate | FMC Biopolymers | 90 | 90 |
| Talc | Luzenac | 180 | 180 |
| Hydroxypropyl methyl cellulose (Pharmacoat 603) | Shin-Etsu | 9 | 9 |
| Purified Water | | 6696 | |
| Total | | 6975 | 279 |

Solid Content of Coating Suspension: 4% w/w
Procedure for Coating Suspension Preparation:
1. Potassium Alginate was weighed and kept under stirring with water for 60 minutes on an overhead stirrer to prepare 2% solution.
2. Hydroxypropyl methyl cellulose was dispersed in 500 gm water using overhead stirrer and then added to potassium alginate solution.
3. Talc was homogenized with remaining amount of water for 30 minutes.
4. Homogenized talc suspension was added to potassium Alginate solution and stirring was continued for further 30 mins.
5. The final prepared suspension was passed through a sieve of 420 microns (40#).
6. This suspension was further sprayed onto pellets in fluid bed processor.

Equipment and in Process Coating Parameters for Pellets:
Instrument used: GPCG 3.1
Silicone tube: 5.0 mm inner diameter
Column height: 15-25 mm
Nozzle bore: 0.8 mm
Filter shaking mode: Asynchronous
Filter shaking: 10 sec
Filter shaking pause: 100 sec
Air flow mode: Auto
Air flow: 150-170 m³/h
Atomisation pressure: 1.0-1.4 bar
Inlet temperature: 51-69° C.
Product temperature: 37° C.-47° C.
Spray rate: 2-19 g/min
Observation:
  Agglomeration of pellets was observed in pH 6.8 buffer.

Example 4C (Comparative)

Potassium Alginate (200-400 cP for 1% w/w Solution) with Crospovidone (25% w.r.t Potassium Alginate)

Coating of 30% potassium alginate
Formula for 30% w/w Polymer Coating on 500 g Pellets

| Ingredient | Manufacturer | Quantity/Batch [g] | Solid content [g] |
|---|---|---|---|
| Potassium alginate | FMC Biopolymers | 150 | 150 |
| Crospovidone (Polyplasdone XL) | ISP technologies Inc. | 37.5 | 37.5 |
| Talc | Luzenac | 300 | 300 |
| Purified Water | | 11700 | |
| Total | | 12187.5 | 487.5 |

Solid Content of Coating Suspension: 4% w/w
Procedure for Coating Suspension Preparation:
1. Potassium Alginate was weighed and kept under stirring with water for 60 minutes on an overhead stirrer to prepare 2% solution.
2. Talc and Polyplasdone XL were homogenized with remaining amount of water for 30 minutes.
3. Homogenized talc suspension was added to Alginate solution of step 1 and stirring was continued for further 30 mins.
4. The final prepared suspension was passed through a sieve of 300 microns (60#).
5. This suspension was further sprayed onto pellets in fluid bed processor.

Equipment and in Process Coating Parameters for Pellets:
Instrument used: GPCG 3.1
Silicone tube: 5.0 mm inner diameter
Column height: 10-20 mm
Nozzle bore: 0.8 mm
Filter shaking mode: Asynchronous
Filter shaking: 10 sec
Filter shaking pause: 100 sec
Air flow mode: Auto
Air flow: 150-200 m³/h
Atomisation pressure: 1.0-1.2 bar
Inlet temperature: 60-70° C.
Product temperature: 46° C.-51° C.
Spray rate: 2-20 g/min
Observation:
  Slight gel formation and agglomeration was observed in pellets in pH 6.8 buffer.

Example 5C (Comparative)

Potassium Alginate (200-400 cP for 1% w/w Solution) with Crospovidone (35% w.r.t Potassium Alginate) and Polysorbate 80 (2% w.r.t Potassium Alginate)

Coating of 25% potassium alginate
Formula for 25% w/w Polymer Coating on 600 g Pellets

| Ingredient | Manufacturer | Quantity/Batch [g] | Solid content [g] |
|---|---|---|---|
| Potassium alginate | FMC Biopolymers | 150 | 150 |
| Crospovidone (Polyplasdone XL) | International Speciality products | 52.5 | 52.5 |
| Polysorbate 80 | Merck KGaA | 3 | 3 |
| Talc | Luzenac | 300 | 300 |
| Purified Water | | 12132 | |
| Total | | 12637.5 | 505.5 |

Solid Content of Coating Suspension: 4% w/w
Procedure for Coating Suspension Preparation:
1. Potassium Alginate was weighed and kept under stirring with water for 60 minutes on an overhead stirrer to prepare 2% solution.
2. Talc and Polyplasdone XL were homogenized with remaining amount of water (in which Polysorbate 80 was previously added) for 30 minutes.
3. Homogenized talc suspension was added to Alginate solution of step 1 and stirring was continued for further 30 mins.
4. The final prepared suspension was passed through a sieve of 300 microns (60#).
5. This suspension was further sprayed onto pellets in fluid bed processor.

Equipment and in Process Coating Parameters for Pellets:
Instrument used: GPCG 3.1
Silicone tube: 5.0 mm inner diameter
Column height: 10-15 mm
Nozzle bore: 0.8 mm
Filter shaking mode: Asynchronous
Filter shaking: 10 sec
Filter shaking pause: 100 sec
Air flow mode: Auto
Air flow: 195-200 m³/h
Atomisation pressure: 1.1 bar
Inlet temperature: 60-65° C.
Product temperature: 45° C.-50° C.
Spray rate: 8-10 g/min
Observation:
  Slight gel formation and agglomeration was observed in pellets in pH 6.8 buffer.

Example 6C (Comparative)

Plain Sodium Alginate (100-300 cP for 2% w/w Solution) with 15% (w.r.t Sodium Alginate) Glycerine as Plasticizer Coating of 70% polymer plain sodium alginate
Formula for 70% w/w Polymer Coating on 600 g Pellets

| Ingredient | Manufacturer | Quantity/Batch [g] | Solid content [g] |
|---|---|---|---|
| KELTONE ® LVCR | FMC Biopolymers | 420 | 420 |
| Talc | Luzenac | 210 | 210 |
| Glycerine | Merck KGaA | 63 | 63 |
| Purified Water | | 16632 | |
| Total | | 17325 | 693 |

Solid Content of Coating Suspension: 4% w/w
Curing parameter: Fluidisation for 2 hrs at 60° C.
Procedure for Coating Suspension Preparation:
1. Sodium Alginate was weighed and kept under stirring with water for 60 minutes on an overhead stirrer to prepare 4% solution.
2. Talc and colour were homogenized with remaining amount of water for 30 minutes.
3. Glycerine was added to the homogenized talc suspension and homogenisation was continued for 10 minutes
4. Homogenized talc suspension was added to Alginate solution and stirring was continued for further 30 mins.
5. The final prepared suspension was passed through a sieve of 420 microns (40#).
6. This suspension was further sprayed onto pellets in fluid bed processor.

Equipment and in Process Coating Parameters for Pellets:
Instrument used: GPCG 3.1
Silicone tube: 5.0 mm inner diameter
Column height: 10-20 mm
Nozzle bore: 0.8 mm
Filter shaking mode: Asynchronous
Filter shaking: 6 sec
Filter shaking pause: 120 sec
Air flow mode: Auto
Air flow: 110-195 m³/h
Atomisation pressure: 1.0-1.4 bar
Inlet temperature: 63-72° C.
Product temperature: 48° C.-51° C.
Spray rate: 2-19 g/min

Example 7C (Comparative)

Plain Sodium Alginate (100-300 cP for 2% w/w Solution

Coating of 180% polymer plain sodium alginate
Formula for 180% w/w Polymer Coating on 600 g Pellets

| Ingredient | Manufacturer | Quantity/Batch [g] | Solid content [g] |
|---|---|---|---|
| KELTONE ® LVCR | FMC Biopolymers | 1080 | 1080 |

-continued

| Ingredient | Manufacturer | Quantity/Batch [g] | Solid content [g] |
|---|---|---|---|
| Talc | Luzenac | 540 | 540 |
| Purified Water | | 38880 | |
| Total | | 40500 | 1620 |

Solid Content of Coating Suspension: 4% w/w
Procedure for Coating Suspension Preparation:
1. Sodium Alginate was weighed and kept under stirring with water for 60 minutes on an overhead stirrer to prepare 4% solution.
2. Talc was homogenized with remaining amount of water for 30 minutes.
3. Homogenized talc suspension was added to Alginate solution and stirring was continued for further 30 mins.
4. The final prepared suspension was passed through a sieve of 420 microns (40#).
5. This suspension was further sprayed onto pellets in fluid bed processor.

Equipment and in Process Coating Parameters for Pellets:
Instrument used: GPCG 3.1
Silicone tube: 5.0 mm inner diameter
Column height: 20-40 mm
Nozzle bore: 0.8 mm
Filter shaking mode: Asynchronous
Filter shaking: 5 sec
Filter shaking pause: 120 sec
Air flow mode: Auto
Air flow: 120-170 m$^3$/h
Atomisation pressure: 1.5-1.6 bar
Inlet temperature: 68-81° C.
Product temperature: 48° C.-57° C.
Spray rate: 2-18 g/min Example 8C (Comparative)

EUDRAGIT® NM 30D: Sodium Alginate (100-300 cP for 2% w/w Solution):1:3

Coating of 100% EUDRAGIT® NM 30D: sodium alginate:: 1:3
Formula for 100% w/w Polymer Coating on 600 g Pellets

| Ingredient | Manufacturer | Quantity/Batch [g] | Solid content [g] |
|---|---|---|---|
| KELTONE ® LVCR | FMC Biopolymers | 450 | 450 |
| EUDRAGIT ® NM 30D | Evonik industries | 500 | 150 |
| Talc | Luzenac | 300 | 300 |
| Purified Water | | 21250 | |
| Total | | 22500 | 900 |

Solid Content of Coating Suspension: 4% w/w
Procedure for Coating Suspension Preparation:
1. Sodium Alginate was weighed and kept under stirring with water for 60 minutes on an overhead stirrer to prepare 4% solution.
2. Talc and colour were homogenized with remaining amount of water for 30 minutes.
3. Homogenized talc suspension was added to Alginate solution and stirring was continued for further 30 mins.
4. EUDRAGIT® NM 30D was added to alginate solution under stirring for 10 minutes
5. The final prepared suspension was passed through a sieve of 420 microns (40#).
6. This suspension was further sprayed onto pellets in fluid bed processor.

Equipment and in Process Coating Parameters for Pellets:
Instrument used: GPCG 3.1
Silicone tube: 5.0 mm inner diameter
Column height: 20-40 mm
Nozzle bore: 0.8 mm
Filter shaking mode: Asynchronous
Filter shaking: 5 sec
Filter shaking pause: 120 sec
Air flow mode: Auto
Air flow: 105-160 m$^3$/h
Atomisation pressure: 1.4-1.6 bar
Inlet temperature: 70-78° C.
Product temperature: 49° C.-57° C.
Spray rate: 2-14 g/min Example 9C (Comparative)

EUDRAGIT® L 30D 55: Sodium Alginate (100-300 cP for 2% w/w Solution::1.:1.5

Coating of 140% EUDRAGIT® L30D 55: Sodium alginate: 1:1.5
Formula for 140% w/w Polymer Coating on 600 g Pellets

| Ingredient | Manufacturer | Quantity/Batch [g] | Solid content [g] |
|---|---|---|---|
| KELTONE ® LVCR | FMC Biopolymers | 504 | 504 |
| EUDRAGIT ® L 30D 55 | Evonik industries | 1119.88 | 336 |
| Talc | Luzenac | 420 | 420 |
| Purified Water | | 29456.12 | |
| Total | | 31500 | 1260 |

Solid Content of Coating Suspension: 4% w/w
Procedure for Coating Suspension Preparation:
1. Sodium Alginate was weighed and kept under stirring with water for 60 minutes on an overhead stirrer to prepare 4% solution.
2. Talc was homogenized with remaining amount of water for 30 minutes.
3. Homogenized talc suspension was added to Alginate solution and stirring was continued for further 30 mins.
4. EUDRAGIT® L 30D 55 was added to alginate solution under stirring for 10 minutes
5. The final prepared suspension was passed through a sieve of 420 microns (40#).
6. This suspension was further sprayed onto pellets in fluid bed processor.

Equipment and in Process Coating Parameters for Pellets:
Instrument used: GPCG 3.1
Silicone tube: 5.0 mm inner diameter
Column height: 20-40 mm
Nozzle bore: 0.8 mm
Filter shaking mode: Asynchronous
Filter shaking: 5 sec
Filter shaking pause: 300 sec Air flow mode: Auto
Air flow: 140-175 m³/h
Atomisation pressure: 1.4-1.5 bar
Inlet temperature: 68-73° C.
Product temperature: 47° C.-52° C.
Spray rate: 2-21 g/min Example 10C (comparative)

EUDRAGIT® L 30D 55: Sodium Alginate
(100-300 cP for 2% w/w Solution): 1:0.5

Coating of 125% EUDRAGIT® L 30D 55: Sodium Alginate::1:0.5
Formula for 125% w/w Polymer Coating on 600 g Pellets

| Ingredient | Manufacturer | Quantity/Batch [g] | Solid content [g] |
|---|---|---|---|
| KELTONE® LVCR | FMC Biopolymers | 250 | 250 |
| EUDRAGIT® L 30D 55 | Evonik industries | 1666.67 | 500 |
| Talc | Luzenac | 375 | 375 |
| Triethyl citrate | Vertellus Specialities Inc. | 25 | 25 |
| Purified Water | | 26433.33 | |
| Total | | 28750 | 1150 |

Solid Content of Coating Suspension: 4% w/w
Procedure for Coating Suspension Preparation:
1. Sodium Alginate was weighed and kept under stirring with water for 60 minutes on an overhead stirrer to prepare 4% solution.
2. Talc was homogenized with remaining amount of water for 20 minutes.
3. Triethyl citrate was added to the homogenised talc suspension and homogenisation was continued for 10 minutes
4. Homogenized talc suspension was added to Alginate solution and stirring was continued for further 30 mins.
5. EUDRAGIT® L 30D 55 was added to alginate solution under stirring for 10 minutes
6. The final prepared suspension was passed through a sieve of 420 microns (40#).
7. This suspension was further sprayed onto pellets in fluid bed processor.
Equipment and in Process Coating Parameters for Pellets:
Instrument used: GPCG 3.1
Silicone tube: 5.0 mm inner diameter
Column height: 20-40 mm
Nozzle bore: 0.8 mm
Filter shaking mode: Asynchronous
Filter shaking: 5 sec
Filter shaking pause: 300 sec
Air flow mode: Auto
Air flow: 130-175 m³/h
Atomisation pressure: 1.4 bar
Inlet temperature: 66-73° C.
Product temperature: 44° C.-50° C.
Spray rate: 2-21 g/min Example 11C (Comparative)

Plain EUDRAGIT® L 30D 55

Coating of 20% EUDRAGIT® L 30D 55
Formula for 20% w/w Polymer Coating on 600 g Pellets

| Ingredient | Manufacturer | Quantity/Batch [g] | Solid content [g] |
|---|---|---|---|
| EUDRAGIT® L 30D 55 | Evonik industries | 400 | 120 |
| Talc | Luzenac | 60 | 60 |
| Triethyl citrate | Vertellus Specialities Inc. | 12 | 12 |
| Purified Water | | 808 | |
| Total | | 1280 | 192 |

Solid Content of Coating Suspension: 15% w/w
Procedure for Coating Suspension Preparation:
1. Talc and Triethyl citrate was homogenized in water for 20 minutes.
2. Homogenized talc and Triethyl citrate suspension was added to EUDRAGIT® L 30D 55 dispersion under stirring using an overhead stirrer and stirring was continued for further 10 mins.
3. The final prepared suspension was passed through a sieve of 420 microns (40#).
4. This suspension was further sprayed onto pellets in fluid bed processor.
Equipment and in Process Coating Parameters for Pellets:
Instrument used: GPCG 3.1
Silicone tube: 5.0 mm inner diameter
Column height: 20-40 mm
Nozzle bore: 0.8 mm
Filter shaking mode: Asynchronous
Filter shaking: 5 sec
Filter shaking pause: 100 sec
Air flow mode: Auto
Air flow: 120-150 m³/h
Atomisation pressure: 1.0-1.1 bar
Inlet temperature: 45-49° C.
Product temperature: 31° C.-33° C.
Spray rate: 2-10 g/min
Example 12C (Comparative) Sodium Alginate (100-300 cP for 2% w/w solution)
Coating of 75% sodium alginate
Example 13C (Comparative) Sodium Alginate (100-300 cP for 2% w/w solution
Coating of 55% sodium alginate
Example 14C (Comparative) Sodium Alginate (100-300 cP for 2% w/w solution
Coating of 10% sodium alginate

Example 12C

Formula for 75% w/w Polymer Coating on 400 g Pellets

| Ingredient | Manufacturer | Quantity/Batch [g] | Solid content [g] |
|---|---|---|---|
| KELTONE ® LVCR | FMC Biopolymers | 300 | 300 |
| Talc | Luzenac | 150 | 150 |
| Purified Water | | 10800 | |
| Total | | 11250 | 450 |

Solid Content of Coating Suspension: 4% w/w
Procedure for Coating Suspension Preparation:
1. Sodium Alginate was weighed and kept under stirring with water for 60 minutes on an overhead stirrer to prepare 4% solution.
2. Talc was homogenized with remaining amount of water for 30 minutes.
3. Homogenized talc suspension was added to Alginate solution and stirring was continued for further 30 mins.
4. The final prepared suspension was passed through a sieve of 420 microns (40#).
5. This suspension was further sprayed onto pellets in fluid bed processor.

Equipment and in Process Coating Parameters for Pellets:
Instrument used: GPCG 1.1
Silicone tube: 5.0 mm inner diameter
Column height: 20-40 mm
Nozzle bore: 0.8 mm
Filter shaking mode: Asynchronous
Filter shaking: 4 sec
Filter shaking pause: 50 sec
Air flow mode: Auto
Air flow: 70-84 CFM
Atomisation pressure: 1.2-1.4 bar
Inlet temperature: 61-65° C.
Product temperature: 47° C.-56° C.
Spray rate: 4-13.5 g/min

Example 13C

Coating of 55% Sodium Alginate

Formula for 55% w/w Polymer Coating on 400 g Pellets

| Ingredient | Manufacturer | Quantity/Batch [g] | Solid content [g] |
|---|---|---|---|
| KELTONE ® LVCR | FMC Biopolymers | 220 | 220 |
| Talc | Luzenac | 110 | 110 |
| Purified Water | | 7920 | |
| Total | | 8250 | 330 |

Solid Content of Coating Suspension: 4% w/w
Procedure for Coating Suspension Preparation, Equipment and in Process Coating Parameters for Pellets Same as Example 12C

Example 14C

Coating of 10% Sodium Alginate

Formula for 10% w/w Polymer Coating on 400 g Pellets

| Ingredient | Manufacturer | Quantity/Batch [g] | Solid content [g] |
|---|---|---|---|
| KELTONE ® LVCR | FMC Biopolymers | 40 | 40 |
| Talc | Luzenac | 20 | 20 |
| Purified Water | | 1440 | |
| Total | | 1500 | 60 |

Solid Content of Coating Suspension: 4% w/w
Procedure for Coating Suspension Preparation, Equipment and in Process Coating Parameters for Pellets Same as Example 12C
Example 15, 16, 17 and 18 (Inventive)
Bilayer Coating
Inner layer: Sodium Alginate (100-300 cP for 2% w/w solution)
Outer layer: EUDRAGIT® L 30D 55
Example 15: Inner layer: 75% Sodium Alginate (30 mg/cm$^2$)
Outer layer: 10% EUDRAGIT® L 30D 55 (4 mg/cm$^2$)
Outer layer 13.33% w.r.t inner layer
Example 16: Inner layer: 55% Sodium Alginate (22 mg/cm$^2$)
Outer layer: 20% EUDRAGIT® L 30D 55 (8 mg/cm$^2$)
Outer layer 36.36% w.r.t inner layer
Example 17: Inner layer: 10% Sodium Alginate (4 mg/cm$^2$)
Outer layer: 70% EUDRAGIT® L 30D 55 (28 mg/cm$^2$)
Outer layer 700% w.r.t inner layer
Example 18: Inner layer: 30% Sodium Alginate (12 mg/cm$^2$)
Outer layer: 40% EUDRAGIT® L 30D 55 (16 mg/cm$^2$)
Outer layer 133.34% w.r.t inner layer

Example 15

Inner Layer

Coating of 75% Sodium Alginate
Formula, Procedure for Coating Suspension Preparation, Equipment and in Process Coating Parameters for Pellets Same as 12C
Outer Layer
Coating of 10% EUDRAGIT® L 30D 55
Formula and Procedure for Coating Suspension Preparation for Pellets Same as Example 11C
Equipment and in Process Coating Parameters for Pellets:
Instrument used: Huttlim Mycrolab
Silicone tube: 2.0 mm inner diameter
Nozzle bore: 0.8 mm
Air flow mode: Auto
Air flow: 19-23 m$^3$/hr
Atomisation pressure: 0.9-1.0 bar
Inlet temperature: 33-39.5° C.
Product temperature: 29° C.-31° C.
Microclimate pressure: 0.6 bar
Spray rate: 0.4-2.0 g/min

Example 16

Inner Layer

Coating of 55% Sodium alginate
Formula and Procedure for Coating Suspension Preparation Equipment and in Process Coating Parameters for Pellets Same as 13C

Outer Layer

Coating of 20% EUDRAGIT® L 30D 55
Formula and Procedure for Coating Suspension Preparation for Pellets Same as Example 11C Equipment and in Process Coating Parameters for Pellets Same as Example 15

Example 17

Inner Layer

Coating of 10% Sodium alginate
Formula and Procedure for Coating Suspension Preparation Equipment and in Process Coating Parameters for Pellets Same as 14C

Outer Layer

Coating of 70% EUDRAGIT® L 30D 55
Formula for 70% w/w Polymer Coating on 600 g Pellets

| Ingredient | Manufacturer | Quantity/Batch [g] | Solid content [g] |
|---|---|---|---|
| EUDRAGIT® L 30D 55 | Evonik industries | 1400 | 420 |
| Talc | Luzenac | 210 | 210 |
| Triethyl citrate | Vertellus Specialities Inc. | 42 | 42 |
| Purified Water | | 2828 | |
| Total | | 4480 | 672 |

Solid Content of Coating Suspension: 15% w/w
Procedure for Coating Suspension Preparation Same as Example 11C
Equipment and in process coating parameters for pellets same as example 11C

Example 18

Coating of 30% Sodium Alginate

Formula for 30% w/w Polymer Coating on 400 g Pellets

| Ingredient | Manufacturer | Quantity/Batch [g] | Solid content [g] |
|---|---|---|---|
| KELTONE® LVCR | FMC Biopolymers | 120 | 120 |
| Talc | Luzenac | 60 | 60 |
| Purified Water | | 2160 | |
| Total | | 2340 | 180 |

Solid Content of Coating Suspension: 4% w/w
Formula, Procedure for Coating Suspension Preparation, Equipment and in Process Coating Parameters for Pellets Same as 13C

Outer Layer

Coating of 40% EUDRAGIT® L 30D 55
Formula for 40% w/w Polymer Coating on 600 g Pellets

| Ingredient | Manufacturer | Quantity/Batch [g] | Solid content [g] |
|---|---|---|---|
| EUDRAGIT® L 30D 55 | Evonik industries | 800 | 240 |
| Talc | Luzenac | 120 | 120 |
| Triethyl citrate | Vertellus Specialities Inc. | 24 | 24 |
| Purified Water | | 1616 | |
| Total | | 2560 | 384 |

Solid Content of Coating Suspension: 15% w/w
Coating Formula, Procedure for Coating Suspension Preparation, Equipment and in Process Coating Parameters Same as Example 11C.

Example 19 (Inventive)

Inner layer: 75% Sodium Alginate (30 mg/cm$^2$)
Outer layer: 20% HPMCAS-LF (8 mg/cm$^2$)
Outer layer 26.67% w.r.t inner layer

Inner Layer

Coating of 75% Sodium alginate
Coating Formula, procedure for coating suspension preparation, equipment and in process coating parameters for inner layer same as example 12C.

Outer Layer

Coating of 20% HPMCAS-LF
Formula for 20% w/w Polymer Coating on 100 g Pellets

| Ingredient | Manufacturer | Quantity/Batch [g] | Solid content [g] |
|---|---|---|---|
| HPMCAS-LF | Shin-Etsu | 20 | 20 |
| Talc | Luzenac | 6 | 6 |
| Triethyl citrate | Vertellus Specialities Inc. | 4 | 4 |
| Sodium lauryl sulphate | Cognis | 0.6 | 0.6 |
| Purified Water | | 275.4 | |
| Total | | 306 | 30.6 |

Solid Content of Coating Suspension: 10% w/w
Procedure for Coating Suspension Preparation:
1. Sodium lauryl sulphate and triethyl citrate were dissolved in water maintained at temperature of below 25° C. using an overhead stirrer and stirring was continued till triethyl citrate was completely dissolved
2. HPMCAS-LF was added to solution of step 1 and stirring was continued for 15 minutes
3. Talc was added to step 1 and stirring was continued for 15 minutes
4. The final prepared suspension was passed through a sieve of 250 microns (60#).
5. This suspension was further sprayed onto pellets in fluid bed processor.
6. Post drying was done at 60° C. for 30 minuets Equipment and in Process Coating Parameters for Pellets:
Instrument used: Huttlin Mycrolab
Silicone tube: 2.0 mm inner diameter
Nozzle bore: 0.8 mm
Air flow mode: Auto Air flow: 18-20 m³/h
Atomisation pressure: 0.8 bar
Inlet temperature: 28° C.
Product temperature: 20° C.-24° C.
Spray rate: 1.6-2.0 g/min Example 20 (Inventive)

Inner layer: 75% Sodium Alginate (30 mg/cm²)

Outer layer: 10% EUDRAGIT® L 100 55 (4 mg/cm²)
Outer layer 13.33% w.r.t inner layer
Inner Layer
Coating of 75% Sodium alginate
Coating Formula, procedure for coating suspension preparation, Equipment and in process coating parameters for inner layer same as example 12C.
Outer Layer
Coating of 10% EUDRAGIT® L 100 55
Formula for 20% w/w Polymer Coating on 300 g Pellets
Preparation of EUDRAGIT®L 30D 55 from EUDRAGIT® L 100 55

| Ingredient | Manufacturer | Quantity/Batch [g] | Solid content [g] |
| --- | --- | --- | --- |
| EUDRAGIT® L 10055 | Evonik industries | 74 | 74 |
| 1NaOH | Merck Ltd. | 25 | 1 |
| Purified Water | | 151 | |
| Total | | 250 | 75 |

74 g EUDRAGIT®L 10055 is present in 250 g suspension
20 g EUDRAGIT®L 10055 is present in 66.67 g suspension
Formula for 20% Coating on 100 g Pellets

| Ingredient | Manufacturer | Quantity/Batch [g] | Solid content [g] |
| --- | --- | --- | --- |
| EUDRAGIT® L 30D 55 | Evonik industries | 66.67 | 20 |
| Talc | Luzenac | 10 | 10 |
| Triethyl citrate | Vertellus Specialities Inc. | 2 | 2 |
| Purified Water | | 134.66 | |
| Total | | 213.33 | 32 |

Solid Content of Coating Suspension: 15% w/w
For 20% coating on 100 g pellets 213.33 g coating suspension is required
Therefore for 10% coating on 80 g pellets 85.332 g suspension is required
Procedure for Coating Suspension Preparation:
1. Talc was homogenized with 100 gm water for 20 minutes.
2. Triethyl citrate was added to the homogenised talc suspension and homogenisation was continued for 10 minutes
3. Homogenized talc suspension was added to EUDRAGIT® L 30D 55 dispersion under stirring for 10 minutes.
4. The final prepared suspension was passed through a sieve of 250 microns (60#).
5. This suspension was further sprayed onto pellets in fluid bed processor.
Equipment and in Process Coating Parameters for Pellets:
Instrument used: Huttlin Mycrolab
Silicone tube: 2.0 mm inner diameter
Nozzle bore: 0.8 mm
Air flow mode: Auto
Air flow: 31-34 m³/h
Atomisation pressure: 1.0 bar
Inlet temperature: 39-41° C.
Product temperature: 31° C.-33° C.
Spray rate: 0.4-0.8 g/min Example 21 (Inventive)

Inner Layer: 75% Sodium Alginate (30 mg/cm²)

Outer layer: 10% EUDRAGIT® FS 30D (4 mg/cm²)
Outer layer 13.33% w.r.t inner layer
Inner Layer
Coating of 75% Sodium alginate
Coating Formula, procedure for coating suspension preparation, Equipment and in process coating parameters for inner layer same as example 12C.
Outer Layer
Coating of 10% EUDRAGIT® FS 30D
Formula for 10% w/w Polymer Coating on 80 g Pellets

| Ingredient | Manufacturer | Quantity/Batch [g] | Solid content [g] |
| --- | --- | --- | --- |
| EUDRAGIT® FS 30D | Evonik industries | 26.67 | 8 |
| Talc | Luzenac | 4 | 4 |
| Triethyl citrate | Vertellus Specialities Inc. | 0.4 | 0.4 |
| Purified Water | | 51.6 | |
| Total | | 82.67 | 12.4 |

Solid Content of Coating Suspension: 15% w/w
Procedure for Coating Suspension Preparation:
1. Talc was homogenized with 40 gm water for 20 minutes.
2. Triethyl citrate was added to the homogenised talc suspension and homogenisation was continued for 10 minutes
3. Homogenized talc suspension was added to EUDRAGIT® FS 30D dispersion under stirring for 10 minutes.
4. The final prepared suspension was passed through a sieve of 250 microns (60#).
5. This suspension was further sprayed onto pellets in fluid bed processor.
Equipment and in Process Coating Parameters for Pellets:
Instrument used: Huttlin Mycrolab
Silicone tube: 2.0 mm inner diameter
Nozzle bore: 0.8 mm
Air flow mode: Auto
Air flow: 31-34 m³/h
Atomisation pressure: 1.0 bar
Inlet temperature: 39-41° C.
Product temperature: 31° C.-33° C.
Spray rate: 0.4-0.8 g/min

Example 22 (Comparative)

Plain EUDRAGIT® FS 30D Coating

Coating of 10% EUDRAGIT® FS 30D (4 mg/cm$^2$)
Coating Formula, Procedure for Coating Suspension Preparation, Equipment and in Process Coating Parameters Same as in Example 21

Example 23 (Inventive)

Inner Layer: 50% Potassium Alginate (20 mg/cm$^2$)

Outer layer: 10% EUDRAGIT® L 30D 55 (4 mg/cm$^2$)
Outer layer 20% w.r.t inner layer
Coating of 50% Potassium alginate
Formula for 50% w/w Polymer Coating on 600 g Pellets

| Ingredient | Manufacturer | Quantity/Batch [g] | Solid content [g] |
|---|---|---|---|
| Potassium alginate (PROTANAL® KF 200 FTS) | FMC Biopolymers | 300 | 300 |
| Talc | Luzenac | 150 | 150 |
| Yellow iron oxide | BASF | 1.5 | 1.5 |
| Purified Water | | 16913.88 | |
| Total | | 17365.38 | 451.5 |

Solid Content of Coating Suspension: 2.6% w/w
Procedure for Coating Suspension Preparation:
1. Potassium alginate alginate was weighed and kept under stirring with water for 60 minutes on an overhead stirrer to prepare 3% solution.
2. Talc was homogenized with remaining amount of water for 30 minutes.
3. Homogenized talc suspension was added to Alginate solution and stirring was continued for further 30 mins.
4. The final prepared suspension was passed through a sieve of 420 microns (40#).
5. This suspension was further sprayed onto pellets in fluid bed processor.

Equipment and in Process Coating Parameters for Pellets:
Instrument used: GPCG 3.1
Silicone tube: 5.0 mm inner diameter
Column height: 20-30 mm
Nozzle bore: 0.8 mm
Filter shaking mode: Asynchronous
Filter shaking: 5 sec
Filter shaking pause: 300 sec
Air flow mode: Auto
Air flow: 130-165 m$^3$/h
Atomisation pressure: 1.4-1.5 bar
Inlet temperature: 65-76° C.
Product temperature: 45° C.-54° C.
Spray rate: 6-18 g/min
Outer Layer
Coating of 10% EUDRAGIT® L 30D 55
Coating Formula, Procedure for Coating Suspension Preparation, Equipment and in Process Coating Parameters Same as Example 11C

Example 24 Inventive)

Inner layer: 55% Ammonium Alginate (22 mg/cm$^2$

Outer layer: 15% EUDRAGIT® L 30D 55 (6 mg/cm$^2$)
Outer layer 27.27% w.r.t inner layer
Coating of 55% Ammonium alginate
Formula for 55% w/w Polymer Coating on 600 g Pellets

| Ingredient | Manufacturer | Quantity/Batch [g] | Solid content [g] |
|---|---|---|---|
| Ammonium alginate (ALGIN® NH-LV) | Kimica corporation | 330 | 330 |
| Talc | Luzenac | 165 | 165 |
| Yellow iron oxide | BASF | 1.65 | 1.65 |
| Purified Water | | 16058.35 | |
| Total | | 16555 | 496.65 |

Solid Content of Coating Suspension: 3% w/w
Procedure for Coating Suspension Preparation:
1. Ammonium alginate was weighed and kept under stirring with water for 60 minutes on an overhead stirrer to prepare 3% solution.
2. Talc was homogenized with remaining amount of water for 30 minutes.
3. Homogenized talc suspension was added to Alginate solution and stirring was continued for further 30 mins.
4. The final prepared suspension was passed through a sieve of 420 microns (40#).
5. This suspension was further sprayed onto pellets in fluid bed processor.

Equipment and in Process Coating Parameters for Pellets:
Instrument used: GPCG 3.1
Silicone tube: 5.0 mm inner diameter
Column height: 20-30 mm
Nozzle bore: 0.8 mm
Filter shaking mode: Asynchronous
Filter shaking: 5 sec
Filter shaking pause: 300 sec
Air flow mode: Auto
Air flow: 130-150 m$^3$/h
Atomisation pressure: 1.4-1.5 bar
Inlet temperature: 61-65° C.
Product temperature: 51° C.-57° C.
Spray rate: 10-16.7 g/min
Outer Layer
Coating of 15% EUDRAGIT® L 30D 55
Coating Formula, Procedure for Coating Suspension Preparation, Equipment and in Process Coating Parameters Same as Example 11C

Example 25 (Inventive)

Bilayer Coating

Inner layer: Sodium Alginate (100-300 cP for 2% w/w solution)
Outer layer: Modified EUDRAGIT® L 30D 55
Inner layer: 55% Sodium Alginate (22 mg/cm$^2$)
Outer layer: 10% Modified EUDRAGIT® L 30D 55 (4 mg/cm$^2$)
Outer layer 18.18% w.r.t inner layer
Inner Layer:
Formula, Procedure of Coating Suspension Preparation & Equipment and in-Process Coating Parameters Same as Example 13C.
Outer Layer:
Coating of 10% Modified EUDRAGIT® L 30D 55
Formula for 20% w/w Polymer Coating on 100 g Pellets

| Ingredient | Manufacturer | Quantity/Batch [g] | Solid content [g] |
|---|---|---|---|
| Modified EUDRAGIT ® L 30D 55 | Evonik industries | 66.66 | 20 |
| Talc | Luzenac | 10 | 10 |
| Triethyl citrate | Vertellus Specialities Inc. | 2 | 2 |
| Purified Water | | 134.67 | |
| Total | | 213.33 | 32 |

Solid Content of Coating Suspension: 15% w/w
Procedure for Coating Suspension Preparation:
1. Talc was homogenized with 85 g of water for 20 minutes.
2. Triethyl citrate was added to the homogenised talc suspension and homogenisation was continued for 10 minutes
3. Homogenized talc suspension was added to Modified EUDRAGIT® L 30D 55 dispersion under stirring using an overhead stirrer and stirring was continued for further 10 mins.
4. The final prepared suspension was passed through a sieve of 420 microns (40#).

This suspension was further sprayed onto pellets in fluid bed processor.
Equipment and in Process Coating Parameters for Pellets:
Instrument used: Huttlin Mycrolab
Silicone tube: 2.0 mm inner diameter
Nozzle bore: 0.8 mm
Air flow mode: Auto
Air flow: 17-19 m³/h
Atomisation pressure: 0.8-0.9 bar
Inlet temperature: 33° C.-36° C.
Product temperature: 29° C.-31° C.
Spray rate: 0.4-1.2 g/min
Lansoprazole Pellets Example 26 (Comparative)

Inner Layer: 40% Sodium Alginate (16 mg/cm²

Outer layer: 10% EUDRAGIT® L 30D 55 (4 mg/cm²)
Outer layer 25% w.r.t inner layer
Inner Layer
Formula for 40% w/w Polymer Coating on 400 g Pellets

| Ingredient | Manufacturer | Quantity/Batch [g] | Solid content [g] |
|---|---|---|---|
| KELTON E ® LVCR | FMC Biopolymers | 160 | 160 |
| Talc | Luzenac | 80 | 80 |
| Purified Water | | 5760 | |
| Total | | 6000 | 240 |

Solid Content of Coating Suspension: 4% w/w
Procedure for Coating Suspension Preparation, Equipment and in Process Coating Parameters for Inner Layer Same as Example 12C.
Outer Layer
Coating of 10% EUDRAGIT® L 30D55
Formula for 10% w/w Polymer Coating on 400 g Pellets

| Ingredient | Manufacturer | Quantity/Batch [g] | Solid content [g] |
|---|---|---|---|
| EUDRAGIT ® L 30D 55 | Evonik industries | 133.33 | 40 |
| Talc | Luzenac | 20 | 20 |
| Triethyl citrate | Vertellus Specialities Inc. | 4 | 4 |
| Purified Water | | 269.33 | |
| Total | | 426.66 | 64 |

Solid Content of Coating Suspension: 15% w/w
Equipment and in Process Coating Parameters Same as Example 11C Example 27 (Inventive)

Inner layer: 40% Sodium Alginate (16 mg/cm²

Outer layer: 20% EUDRAGIT® L 30D 55 (8 mg/cm²)
Outer layer 50% w.r.t inner layer
Inner Layer
Formula, Procedure for Coating Suspension Preparation, Equipment and in Process Coating Parameters for Inner Layer Same as Example 26
Outer Layer
Coating of 20% EUDRAGIT® L 30D55
Formula, Procedure for Coating Suspension Preparation, Equipment and in Process Coating Parameters for Inner Layer Same as Example 11C.

Example 28 (Comparative)

Inner Layer: 5% EUDRAGIT® L 100 55
Neutralized to PH 6

Outer layer: 30% EUDRAGIT® L 30D 55
Inner Layer
Part 1: Preparation of EUDRAGIT® L 100 55 Dispersion from EUDRAGIT® L 100 55

| Ingredient | Manufacturer | Quantity/Batch [g] | Solid content [g] |
|---|---|---|---|
| EUDRAGIT ® L 10055 | Evonik industries | 74 | 74 |
| 1N sodium hydroxide | Merck Ltd. | 25 | 1 |
| Purified Water | | 151 | |
| Total | | 250 | 75 |

Procedure for Preparation of 1N Sodium Hydroxide Solution
10 g sodium hydroxide was weighed accurately and dissolved in 250 g water
Neutralization of EUDRAGIT L 100 55
1) EUDRAGIT® L 100-55 was added slowly into the water and stir for 5 minutes using an overhead stirrer
2) 1N NaOH was added slowly into the EUDRAGIT® suspension and stirring was continued for about 30 minutes.
3) The dispersion of step 2 was used as EUDRAGIT®L 100-55 dispersion in Part 2

74 g EUDRAGIT® L 10055 is present in 250 g suspension
40 g EUDRAGIT® L 10055 is present in 135.14 g suspension Part 2: Formula for 20% Coating on 200 g Pellets

| Ingredient | Manufacturer | Quantity/ Batch [g] | Solid content [g] |
|---|---|---|---|
| EUDRAGIT ® L 100 55 dispersion | Evonik industries | 135.14 | 40 |
| Talc | Luzenac | 20 | 20 |
| Triethyl citrate | Vertellus Specialities Inc. | 4 | 4 |
| Purified Water | | 267.53 | |
| Total | | 426.67 | 64 |

Solid Content of Coating Suspension: 15% w/w
For 20% coating on 200 g pellets 426.67 g coating suspension is required
Therefore for 5% coating on 50 g pellets 26.67 g suspension is required Procedure for Coating Suspension Preparation:
1. Talc was homogenized with 200 gm water for 20 minutes.
2. Triethyl citrate was added to the homogenised talc suspension and homogenisation was continued for 10 minutes
3. Homogenized talc suspension was added to EUDRAGIT® L 30D 55 dispersion under stirring for 10 minutes.
4. pH of EUDRAGIT® L 30D 55 suspension was adjusted to 6.0 with 1N sodium hydroxide solution.
5. The final prepared suspension was passed through a sieve of 250 microns (60#).
6. This suspension was further sprayed onto pellets in fluid bed processor.

Equipment and in Process Coating Parameters for Pellets:
Instrument used: Huttlin Mycrolab
Silicone tube: 2.0 mm inner diameter
Nozzle bore: 0.8 mm
Air flow mode: Auto
Air flow: 19-21 m$^3$/h
Atomisation pressure: 1.0-1.2 bar
Inlet temperature: 47-56° C.
Product temperature: 39° C.-48° C.
Spray rate: 0.4 g/min Outer Layer
30% EUDRAGIT L 30D 55 coating
Formula for 20% Coating on 200 g Pellets

| Ingredient | Manufacturer | Quantity/ Batch [g] | Solid content [g] |
|---|---|---|---|
| EUDRAGIT ® L 100 55 dispersion | Evonik industries | 135.14 | 40 |
| Talc | Luzenac | 20 | 20 |
| Triethyl citrate | Vertellus Specialities Inc. | 4 | 4 |
| Purified Water | | 267.53 | |
| Total | | 426.67 | 64 |

For 20% coating on 200 g pellets 426.67 g coating suspension is required
Therefore for 30% coating on 50 g pellets 160.01 g suspension is required Equipment and in Process Coating Parameters for Pellets:
Instrument used: Huttlin Mycrolab
Silicone tube: 2.0 mm inner diameter
Nozzle bore: 0.8 mm
Air flow mode: Auto
Air flow: 21-22 m$^3$/h
Atomisation pressure: 0.9-1.2 bar
Inlet temperature: 34-40° C.
Product temperature: 29° C.-32° C.
Spray rate: 0.4-1.6 g/min Example 29 (Comparative)

Inner Layer: 5% EUDRAGIT® L 100 55 Neutralized to PH 6.0+20% Trisodium Citrate

Outer layer: 10% EUDRAGIT® L 30D 55
Inner Layer
Formula for 10% w/w Polymer Coating on 300 g Pellets

| Ingredient | Manufacturer | Quantity/ Batch [g] | Solid content [g] |
|---|---|---|---|
| EUDRAGIT ® L 30D 55 | Evonik industries | 100 | 30 |
| Trisodium citrate | Merck Ltd. | 6 | 6 |
| Triethyl citrate | Vertellus Specialities Inc. | 3 | 3 |
| Talc | Luzenac | 15 | 15 |
| 1N NaOH | Merck Ltd. | 60 | 2.4 |
| Purified Water | | 416 | |
| Total | | 600 | 56.4 |

Solid Content: 9.4%
For 5% Coating on 50 g Pellets 50 g Coating Suspension Sprayed Procedure for Coating Suspension Preparation:
1. Talc was homogenized with 200 g water for 20 minutes.
2. Triethyl citrate was added to the homogenised talc suspension and homogenisation was continued for 10 minutes
3. Sodium citrate was dissolved in 60.0 g water and added to EUDRAGIT® L 30D 55 dispersion under stirring using an overhead stirrer.
4. Homogenised talc dispersion was added to EUDRAGIT® L 30D 55 under stirring
5. pH of EUDRAGIT® L 30D 55 suspension was adjusted to 6.0 with 1N sodium hydroxide solution.
6. The final prepared suspension was passed through a sieve of 250 microns (60#).
7. This suspension was further sprayed onto pellets in fluid bed processor.

Equipment and in Process Coating Parameters for Pellets:
Instrument used: Huttlin Mycrolab
Silicone tube: 2.0 mm inner diameter
Nozzle bore: 0.8 mm
Air flow mode: Auto
Air flow: 20-22 m$^3$/h
Atomisation pressure: 1.1-1.2 bar
Inlet temperature: 62° C.
Product temperature: 50-54° C.
Spray rate: 0.4 g/min
Outer layer: 10% EUDRAGIT® L 30D 55

Coating Formula, Calculation, Procedure for Coating Suspension Preparation, Coating Parameters Same as Example 28 (Part 2)
For 10% Coating on 50 g Pellets 53.33 g Coating Suspension is Required
Metoprolol Pellets

Example 30C (Comparative)

Sodium Alginate (100-300 cP for 2% w/w Solution

Coating of 75% sodium alginate (30 mg/cm$^2$)

Example 31C (Comparative)

Sodium Alginate (100-300 cP for 2% w/w Solution

Coating of 100% sodium alginate (40 mg/cm$^2$)

Example 32C (Comparative)

Sodium Alginate (100-300 cP for 2% w/w Solution

Coating of 120% sodium alginate (48 mg/cm$^2$)
Formula for 120% w/w Polymer Coating on 600 g Pellets
Same for Example 30C, 31C and 32C

| Ingredient | Manufacturer | Quantity/Batch [g] | Solid content [g] |
|---|---|---|---|
| KELTONE ® LVCR | FMC Biopolymers | 720 | 720 |
| Talc | Luzenac | 360 | 360 |
| Purified Water | | 25920 | |
| Total | | 27000 | 1080 |

Solid Content of Coating Suspension: 4% w/w
Procedure for Coating Suspension Preparation:
1. Sodium Alginate was weighed and kept under stirring with water for 60 minutes on an overhead stirrer to prepare 4% solution.
2. Talc was homogenized with remaining amount of water for 30 minutes.
3. Homogenized talc suspension was added to Alginate solution and stirring was continued for further 30 mins.
4. The final prepared suspension was passed through a sieve of 420 microns (40#).
5. This suspension was further sprayed onto pellets in fluid bed processor.
Equipment and in Process Coating Parameters for Pellets: Same as Example 7C

Example 33C (Comparative)

Drug used: Metoprolol succinate pellets
Bilayer Coating
Inner layer: 100% Sodium Alginate (40 mg/cm$^2$)
Outer layer: 10% EUDRAGIT® L 30D 55 (4 mg/cm$^2$)
Outer layer 10% w.r.t inner layer
Inner Layer
Keltone LVCR Coating:
Formula
Formula for 100% w/w Polymer Coating on 600 g Pellets

| Ingredient | Manufacturer | Quantity/Batch [g] | Solid content [g] |
|---|---|---|---|
| KELTONE ® LVCR | FMC Biopolymers | 600 | 600 |
| Talc | Luzenac | 300 | 300 |
| Purified Water | | 21600 | |
| Total | | 22500 | 900 |

Solid Content of Coating Suspension: 4% w/w
Procedure for Coating Suspension Preparation, Equipment and in Process Coating Parameters Same as Example 7C.
Outer Layer
10% EUDRAGIT® L 30D 55 Coating
Coating Formula, Procedure for Coating Suspension Preparation, Equipment and in Process Coating Parameters for Inner Layer and Outer Layer Same as Example 15.

Example 34 (Inventive)

Drug used: Metoprolol succinate pellets
Bilayer Coating
Inner layer: 100% Sodium Alginate (40 mg/cm$^2$)
Outer layer: 20% EUDRAGIT® L 30D 55 (8 mg/cm$^2$)
Outer layer 20% w.r.t inner layer
Inner Layer
Keltone LVCR coating:
Formula, Procedure for Coating Suspension Preparation, Equipment and in Process Coating Parameters Same as Example 33.
Outer Layer
EUDRAGIT® L 30D 55 Coating
Coating Formula, Procedure for Coating Suspension Preparation, Equipment and in Process Coating Parameters for Inner Layer and Outer Layer Same as Example 16.

Example 35 (Inventive)

Drug used: Metoprolol succinate pellets
Bilayer Coating
Inner layer: 75% Sodium Alginate (30 mg/cm$^2$)
Outer layer: 20% EUDRAGIT® L 30D 55 (8 mg/cm$^2$)
Outer layer 26.67% w.r.t inner layer
Inner Layer
Keltone LVCR Coating:
Formula for Coating Suspension, Procedure for Coating Suspension Preparation, Equipment and in Process Coating Parameters Same as Example 33.
Outer Layer
20% EUDRAGIT® L 30D 55 Coating
Coating Formula, Procedure for Coating Suspension Preparation, Equipment and in Process Coating Parameters for Inner Layer and Outer Layer Same as Example 16.

Minitablet Coating

Example 36 (Inventive)

Inner Layer: 40% Sodium Alginate (18 mg/cm$^2$

Outer layer: 10% EUDRAGIT® L 30D 55 (6 mg/cm$^2$)
Outer layer 25% w. r.t inner layer
Inner Layer
Keltone LVCR Coating:
Formula for Coating Suspension Same as in Example 27
Procedure for Coating Suspension Preparation, Equipment and in Process Coating Parameters Same as Example 27.
Outer Layer
EUDRAGIT® L 30 D 55 Coating:
Formula for Coating Suspension Same as in Example 15.
Procedure for Coating Suspension Preparation, Equipment and in Process Coating Parameters Same as Example 15.

Example 37 (Inventive)

Inner Layer: 25% Sodium Alginate (12 mg/cm$^2$

Outer layer: 15% EUDRAGIT® L 30D 55 (10 mg/cm$^2$)
Outer layer 60% w.r.t inner layer
Inner Layer
Keltone LVCR Coating:
Formula for Coating Suspension Preparation
Formula for 25% w/w Polymer Coating on 400 g Pellets

| Ingredient | Manufacturer | Quantity/Batch [g] | Solid content [g] |
|---|---|---|---|
| KELTONE ® LVCR | FMC Biopolymers | 100 | 100 |
| Talc | Luzenac | 50 | 50 |
| Purified Water | | | 3600 |
| Total | | 150 | 3750 |

Solid Content of Coating Suspension: 4% w/w
Procedure for Coating Suspension Preparation, Equipment and in Process Coating Parameters Same as Example 15.
Outer Layer
EUDRAGIT® L 30 D 55 Coating:
Formula for Coating Suspension Same as in Example 15
Procedure for Coating Suspension Preparation, Equipment and in Process Coating Parameters Same as Example 15.

Example 38 (Comparative)

Inner Layer: 40% Sodium Alginate (18 mg/cm$^2$

Outer layer: 4% EUDRAGIT® L 30D 55 (3 mg/cm$^2$)
Outer layer 10% w.r.t inner layer
Inner Layer
Keltone LVCR Coating:
Formula for Coating Suspension Same as in Example 27
Procedure for Coating Suspension Preparation, Equipment and in Process Coating Parameters Same as Example 15.
Outer Layer
4% EUDRAGIT® L 30 D 55 Coating:
Formula for 20% Coating on 100 g Pellets

| Ingredient | Manufacturer | Quantity/Batch [g] | Solid content [g] |
|---|---|---|---|
| EUDRAGIT ® L 30D 55 | Evonik industries | 66.67 | 20 |
| Talc | Luzenac | 10 | 10 |
| Triethyl citrate | Vertellus Specialities Inc. | 2 | 2 |
| Purified Water | | 134.66 | |
| Total | | 213.33 | 32 |

Solid Content:
For 20% coating on 100 g pellets 213.33 g coating suspension is required
Therefore for 4% coating on 70 g pellets 42.67 g suspension is required
Procedure for Coating Suspension Preparation, Equipment and in Process Coating Parameters Same as Example 15.

Example 39 (Inventive)

Inner Layer: 40% Sodium Alginate (18 mg/cm$^2$

Outer layer: 7% EUDRAGIT® L 30D 55 (4 mg/cm$^2$)
Outer layer 17.5% w.r.t inner layer
Inner Layer
Keltone LVCR Coating:
Formula for Coating Suspension Same as in Example 27
Procedure for Coating Suspension Preparation, Equipment and in Process Coating Parameters Same as Example 15.
Results:
Resistance to alcohol dose dumping was observed with coating level of 40% with 1% drug release after 120 minutes in 40% alcoholic HCl.
Outer Layer
7% EUDRAGIT® L 30 D 55 Coating:
7% coating on 70 g pellets 52.26 g suspension sprayed
Procedure for Coating Suspension Preparation, Equipment and in Process Coating Parameters Same as Example 15.

Capsule Coating

Example 40 (Inventive)

Bilayer Coating

Inner layer: 5.17% (6 mg/cm$^2$) Sodium Alginate
Outer layer: 4.97% (6 mg/cm$^2$) EUDRAGIT® L 30D 55
Outer layer 96.13% w.r.t inner layer
Inner layer
Core used: Hard gelatin capsule filled with caffeine pellets
Capsule shape: Oblong
Capsule size: 1
Formula for 8% w/w Polymer Coating on 500 g Capsules

| Ingredient | Manufacturer | Quantity/Batch [g] | Solid content [g] |
|---|---|---|---|
| KELTONE ® LVCR | FMC Biopolymers | 40 | 40 |

-continued

| Ingredient | Manufacturer | Quantity/Batch [g] | Solid content [g] |
|---|---|---|---|
| Talc | Luzenac | 20 | 20 |
| Purified Water | | 1440 | |
| Total | | 1500 | 60 |

Total Solid Content: 4% w/w
Calculations:
Coating level: 6 mg/cm$^2$
Weight of capsule: 494.72 mg
Surface area of capsule: 410.0 mm$^2$ $$\% \text{ Polymer} = \frac{\text{Coating level (mg/cm}^2\text{)} \times \text{Surface area}}{\text{Weight of capsule}}$$

$$= \frac{6 \times 410}{494.72}$$

$$= 4.97\% \ w/w$$

40.0 gm polymer is present in 60.0 gm total solid which is present in 1500.0 gm coating suspension
Therefore, 4.97 gm polymer is present in 7.46 gm total solid which is present in 186.5 gm coating suspension
For 4.97% coating on 100.0 gm capsules 186.5 gm coating suspension is required
Therefore
For 4.97% coating opn 500.0 gm capsules 932.5 gm coating suspension is required

| | | | Required weight gain | |
|---|---|---|---|---|
| % Polymer (g) | Total solid (g) | Required suspension (g) | Per capsule (mg) | 20 capsule (g) |
| 4.97 | 7.46 | 932.5 | 531.63 | 10.63 |

Procedure for Coating Suspension Preparation
Same as Example 16, 17 and 18
Instrument Used: Neocota
Coating Parameters:
Spraying Parameters:
Nozzle bore: 1.0 mm
Coating pan: 14 inch
Baffles: Present
Silicon tube od/id: 6/3 mm
Exhaust: ON
Blower: ON
Spray air pressure: 1.5 bar
Inprocess Parameters
Pan rpm range: 7-8 rpm
Pump rpm range: 6-8 rpm
Inlet air temperature: 37-45° C.
Product temperature: 24-27° C.
Exhaust temperature: 30-33° C.
Spray rate range: 3.55-4.73 g/min
Drying Parameters
Pan rpm range: 4 rpm
Inlet air temperature: 32-33° C.
Product temperature: 29-30° C.
Exhaust temperature: 31-32° C.

Outer Layer
Core used: Keltone LVCR coated hard gelatin capsule filled with caffeine pellets
Capsule shape: Oblong
Capsule size: 1
Formula for 10% w/w Polymer Coating on 600 g Capsules

| Ingredient | Manufacturer | Quantity/Batch [g] | Solid content [g] |
|---|---|---|---|
| EUDRAGIT® L 30 D55 | Evonik industies | 166.67 | 50 |
| Triethyl citrate | Vertellus Specialities Inc. | 10.0 | 10 |
| Talc | Luzenac | 25.0 | 25 |
| Water | | 1498.33 | |
| | | 1700.0 | 85 |

Total Solid Content: 5% w/w
Calculation:
Weight of capsule: 531.63 mg
Surface area of capsule: 410 mm$^2$

| Coating level (mg/cm$^2$) | % Polymer (g) | % Total solid (g) | Required suspension (g) | Weight gain Per capsule (mg) | Weight gain 20 capsule (g) |
|---|---|---|---|---|---|
| 6 | 4.63 | 7.87 | 787.0 | 573.47 | 11.47 |

Procedure for Coating Suspension Preparation Same as Example 11C
Instrument Used: Neocota
Coating Parameters:
Spraying Parameters:
Nozzle bore: 1.0 mm
Coating pan: 14 inch
Baffles: Present
Silicon tube od/id: 6/3 mm
Exhaust: ON
Blower: ON
Spray air pressure: 1 bar
Inprocess Parameters
Pan rpm range: 8 rpm
Pump rpm range: 6 rpm
Inlet air temp.: 32-42° C.
Product temp.: 22-29° C.
Exhaust temp.: 27-35° C.
Spray rate range: 2.94-3.30 g/min
Drying Parameters
Pan rpm range: 4 rpm
Inlet air temperature: 32-33° C.
Product temperature: 28-29° C.
Exhaust temperature: 31-32° C.

Example 41 (Inventive)

Bilayer Coating

Inner layer: 5.17% (6 mg/cm$^2$) Sodium Alginate
Outer layer: 0.8% (1 mg/cm$^2$) EUDRAGIT® L 30D 55
Outer layer 15.47% w.r.t inner layer
Inner Layer
Core used: Hard gelatin capsule filled with caffeine pellets
Capsule shape: Oblong Capsule size: 1
Formula for 8% w/w Polymer Coating on 500 g Capsules

| Ingredient | Manufacturer | Quantity/ Batch [g] | Solid content [g] |
|---|---|---|---|
| KELTONE ® LVCR | FMC Biopolymers | 40 | 40 |
| Talc | Luzenac | 20 | 20 |
| Purified Water | | 1940 | |
| Total | | 2000 | 60 |

Total Solid Content: 3% w/w
Calculations:
Coating level: 6 mg/cm$^2$
Weight of capsule: 475.41 mg
Surface area of capsule: 410.0 mm $$\% \text{ Polymer} = \frac{\text{Coating level (mg/cm}^2) \times \text{Surface area}}{\text{Weight of capsule}}$$

$$= \frac{6 \times 410}{475.41}$$

$$= 5.17\% \ w/w$$

40.0 gm polymer is present in 60.0 gm total solid which is present in 2000.0 gm coating suspension
Therefore,
5.17 gm polymer is present in 7.76 gm total solid which is present in 258.67 gm coating suspension
For 5.17% coating on 100.0 gm capsules 258.67 gm coating suspension is required
Therefore
For 5.17% coating opn 500.0 gm capsules 1293.35 gm coating suspension is required

| | | | Required weight gain | |
|---|---|---|---|---|
| % Polymer (g) | % Total solid (g) | Required suspension (g) | Per capsule (mg) | 20 capsule (g) |
| 5.17 | 7.76 | 1293.35 | 512.30 | 10.25 |

Procedure for Coating Suspension Preparation Same as Example 16, 17 & 18.
Instrument Used: Neocota
Coating Parameters:
Spraying Parameters:
Nozzle bore: 1.0 mm
Coating pan: 14 inch
Baffles: Present
Silicon tube od/id: 6/3 mm
Exhaust: ON
Blower: ON
Spray air pressure: 1.5 bar
Inprocess Parameters
Pan rpm range: 7-8 rpm
Pump rpm range: 6-8 rpm
Inlet air temperature: 37-45° C.
Product temperature: 24-27° C.
Exhaust temperature: 30-33° C.
Spray rate range: 3.55-4.73 g/min
Drying Parameters
Pan rpm range: 4 rpm
Inlet air temperature: 32-33° C.
Product temperature: 29-30° C.
Exhaust temperature: 31-32° C.
Outer Layer
Core used: Keltone coated hard gelatin capsule filled with caffeine pellets
Capsule shape: Oblong
Capsule size: 1
Formula for 2% w/w Polymer Coating on 500 g Capsules

| Ingredient | Manufacturer | Quantity/ Batch [g] | Solid content [g] |
|---|---|---|---|
| EUDRAGIT ® L 30 D55 | Evonik industies | 33.33 | 10.0 |
| Triethyl citrate | Vertellus Specialities Inc. | 2.0 | 2.0 |
| Talc | Luzenac | 5.0 | 5.0 |
| Water | | 526.34 | 17 |

Total Solid Content: 3% w/w
Coating Formula,
Calculation:
Coating level: 1 mg/cm$^2$
Weight of capsule: 514.0 mg
Surface area of capsule: 410 me
% Polymer=0.8% w/w

| Coating level (mg/cm$^2$) | % Polymer (g) | % Total solid (g) | Required suspension (g) | Weight gain Per capsule (mg) | 20 capsule (g) |
|---|---|---|---|---|---|
| 1 | 0.80 | 1.36 | 226.65 | 520.99 | 10.42 |

Procedure for Coating Suspension Preparation Same as Example 11C
Instrument Used: Neocota
Coating Parameters:
Spraying Parameters:
Nozzle bore: 1.0 mm
Coating pan: 14 inch
Baffles: Present
Silicon tube od/id: 6/3 mm
Exhaust: ON
Blower: ON
Spray air pressure: 1 bar
Inprocess Parameters
Pan rpm range: 8 rpm
Pump rpm range: 6 rpm
Inlet air temperature: 37-41° C.
Product temperature: 23-26° C.
Exhaust temperature: 29-32° C.
Spray rate range: 3.30 g/min
Drying Parameters
Pan rpm range: 4 rpm
Inlet air temperature: 32-33° C.
Product temperature: 28-29° C.
Exhaust temperature: 31-32° C.

Example 42 (Inventive)

Bilayer Coating

Inner layer: 3.5% (4 mg/cm$^2$) Sodium Alginate
Outer layer: 0.8% (1 mg/cm$^2$) EUDRAGIT® L 30D 55

Outer layer 22.86% w.r.t inner layer
Inner Layer
3.5% w/w Sodium Alginate
Core used: Hard gelatin capsule filled with caffeine pellets
Capsule shape: Oblong
Capsule size: 1
Coating Formula, Calculation, Procedure for Coating Suspension Preparation, Coating Parameters Same as Example 41
Outer layer: 0.8% w/w EUDRAGIT® L 30D 55
Coating Formula, Calculation, Procedure for Coating Suspension Preparation, Coating Parameters Same as Example 11C

Example 43 (Inventive)

Drug used: Duloxetine hydrochloride pellets
Bilayer Coating
Inner layer: 60% Sodium Alginate
Outer layer: 15% EUDRAGIT® L 30D 55
Outer layer 25% w.r.t inner layer
Inner Layer
Keltone LVCR coating:
Inner Layer
Formula for 60% w/w Polymer Coating on 600 g Pellets

| Ingredient | Manufacturer | Quantity/Batch [g] | Solid content [g] |
|---|---|---|---|
| KELTONE ® LVCR | FMC Biopolymers | 360 | 360 |
| Talc | Luzenac | 180 | 180 |
| Purified Water | | 12960 | |
| Total | | 13500 | 540 |

Solid Content of Coating Suspension: 4% w/w
Procedure for Coating Suspension Preparation, Equipment and in Process Coating Parameters for inner layer same as example 7C.
Formula for Coating Suspension, Procedure for Coating Suspension Preparation, Equipment and in process coating parameters same as example 15.
Outer Layer
EUDRAGIT® L 30D 55 Coating
Coating Formula, Procedure for Coating Suspension Preparation, Equipment and in Process Coating Parameters for Inner Layer and Outer Layer Same as Example 33C

Caffeine Tablets

Example 44 (Inventive)

Bilayer Coating

Inner layer: 1.78% (2 mg/cm$^2$) Sodium Alginate
Outer layer: 1.78% (2 mg/cm$^2$) EUDRAGIT® L 30D 55
Outer layer: 100% w.r.t inner layer
Inner Layer
Core used: Caffeine Tablets
Tablet shape: Circular
Tablet size: 11 mm
Formula for 5% w/w Polymer Coating on 400 g Tablets

| Ingredient | Manufacturer | Quantity/Batch [g] | Solid content [g] |
|---|---|---|---|
| KELTONE ® LVCR | FMC Biopolymers | 20 | 20 |
| Talc | Luzenac | 10 | 10 |
| Purified Water | | 720 | |
| Total | | 750 | 30 |

Total Solid Content: 4% w/w
Calculations:
Coating level: 2 mg/cm$^2$
Weight of Tablet: 398 mg
Surface area of tablet: 354.26 mm$^2$ $$\% \text{ Polymer} = \frac{\text{Coating level (mg/cm}^2\text{)} \times \text{Surface area}}{\text{Weight of tablet}}$$

$$= \frac{2 \times 354.26}{398}$$

$$= 1.78\% \ w/w$$

20.0 gm polymer is present in 30.0 gm total solid which is present in 750.0 gm coating suspension
Therefore,
1.78 gm polymer is present in 2.67 gm total solid which is present in 66.75 gm coating suspension
For 1.78% coating on 100.0 gm tablets 66.75 gm coating suspension is required
Therefore
For 1.78% coating opn 330.0 gm tablets 220.28 gm coating suspension is required

| % Polymer (g) | % Total solid (g) | Required suspension (g) | Required weight gain Per Tablet (mg) | 20 Tablet(g) |
|---|---|---|---|---|
| 1.78 | 2.67 | 220.28 | 408.63 | 8.17 |

Procedure for Coating Suspension Preparation
Same as Example 7C
Instrument Used: Coating Pan
Coating Parameters:
Spraying Parameters:
Nozzle bore: 1.0 mm
Coating pan size: 12 inch
Baffles: Present
Silicon tube od/id: 5/3 mm
Exhaust: ON
Blower: ON
Spray air pressure: 1.0 bar
Inprocess Parameters
Pan rpm range: 15 rpm
Pump rpm range: 1-2 rpm
Inlet air temperature: 48-52° C.
Product temperature: 37-41° C.
Spray rate range: 2.9-5.8 g/min Outer Layer
Core used: Keltone LVCR caffeine Tablets
Tablet shape: Circular
Tablet size: 11 mm
Formula for 5% w/w Polymer Coating on 400 g Tablets

| Ingredient | Manufacturer | Quantity/Batch [g] | Solid content [g] |
|---|---|---|---|
| EUDRAGIT ® L 30 D55 | Evonik industies | 66.67 | 20 |
| Triethyl citrate | Vertellus Specialities Inc. | 2 | 2 |
| Talc | Luzenac | 10 | 10 |
| Water | | 561.33 | |
| | | 640 | 32 |

Total Solid Content: 5% w/w
Calculation:
Coating level: 2 mg/cm$^2$
Weight of Tablets: 409 mg
Surface area of Tablets: 354.26 mm$^2$ $$\% \text{ Polymer} = \frac{\text{Coating level (mg/cm}^2) \times \text{Surface area}}{\text{Weight of tablet}}$$

$$= \frac{2 \times 354.26}{409}$$

$$= 1.73\% \ w/w$$

20.0 gm polymer is present in 32.0 gm total solid which is present in 640.0 gm coating suspension
Therefore,
1.73 gm polymer is present in 2.77 gm total solid which is present in 55.4 gm coating suspension
For 1.73% coating on 100.0 gm tablets 55.4 gm coating suspension is required
Therefore
For 1.73% coating opn 307.0 gm tablets 170 gm coating suspension is required

| Coating level (mg/cm$^2$) | % Polymer (g) | % Total solid (g) | Required suspension (g) | Weight gain Per tablet (mg) | Weight gain 20 tablets (g) |
|---|---|---|---|---|---|
| 2 | 1.73 | 2.77 | 170 | 420.34 | 8.41 |

Procedure for Coating Suspension Preparation Same as Example 11C
Instrument Used: Coating Pan
Coating Parameters:
Spraying Parameters:
Nozzle bore: 1.0 mm
Coating pan size: 12 inch
Baffles: Present
Silicon tube od/id: 5/3 mm
Exhaust: ON
Blower: ON
Spray air pressure: 1 bar
Inprocess Parameters
Pan rpm range: 19 rpm
Pump rpm range: 1 rpm
Inlet air temp.: 39-43° C.
Product temp.: 28-32° C.
Spray rate range: 2.22 g/min Example 45 (Inventive)

Bilayer Coating

Inner layer: 1.78% (2 mg/cm$^2$) Sodium Alginate
Outer layer: 0.87% (1 mg/cm$^2$) EUDRAGIT® L 30D 55
Outer layer: 50% w.r.t inner layer
Inner Layer
Core used: Caffeine Tablets
Tablet shape: Circular
Tablet size: 11 mm
Formula, Calculations, Procedure for Coating Suspension Preparation, Coating Parameters Same as Example 44
Outer Layer
Core used: Keltone LVCR caffeine Tablets
Tablet shape: Circular
Tablet size: 11 mm
Formula for 5% w/w Polymer Coating on 400 g Tablets

| Ingredient | Manufacturer | Quantity/Batch [g] | Solid content [g] |
|---|---|---|---|
| EUDRAGIT ® L 30 D55 | Evonik industies | 66.67 | 20 |
| Triethyl citrate | Vertellus Specialities Inc. | 2 | 2 |
| Talc | Luzenac | 10 | 10 |
| Water | | 561.33 | |
| | | 640 | 32 |

Total Solid Content: 5% w/w
Calculation:
Coating level: 1 mg/cm$^2$
Weight of Tablets: 409 mg
Surface area of Tablets: 354.26 mm$^2$ $$\% \text{ Polymer} = \frac{\text{Coating level (mg/cm}^2) \times \text{Surface area}}{\text{Weight of tablet}}$$

$$= \frac{1 \times 354.26}{409}$$

$$= 0.87\% \ w/w$$

20.0 gm polymer is present in 32.0 gm total solid which is present in 640.0 gm coating suspension
Therefore, 0.87 gm polymer is present in 1.39 gm total solid which is present in 27.8 gm coating suspension
For 0.87% coating on 100.0 gm tablets 27.8 gm coating suspension is required
Therefore
For 0.87% coating opn 307.0 gm tablets 85.35 gm coating suspension is required

| Coating level (mg/cm$^2$) | % Polymer (g) | % Total solid (g) | Required suspension (g) | Weight gain Per tablet (mg) | Weight gain 20 tablets (g) |
|---|---|---|---|---|---|
| 1 | 0.87 | 1.39 | 85.35 | 414.67 | 8.29 |

Procedure for Coating Suspension Preparation Same as Example 11C
Instrument used: Coating Pan
Coating Parameters Same as Example 44

| | | | CAFFEINE PELLETS | | | | | |
|---|---|---|---|---|---|---|---|---|---|
| | | | Amount | | | API Release | | | |
| Example No. | Inner/ Outer layer | Polymer Coating Type | Polymer Coating [%] | Ratio | Other excipients | Enteric pH 1.2 - 120 min | Buffer pH 5.5 45 min | Buffer pH 6.8 45 min | passed/ failed |
| 1C | — | Potassium Alginate | 30 | — | Aerosil (10%), Talc (150%) | 25 | — | 57 (60 min) agglomeration of pellets | Fails |
| 2C | — | Potassium Alginate | 30 | — | Sipernate (15%), Talc (200%) | 19 | — | 54(60 min) agglomeration of pellets | Fails |
| 3C | — | Potassium Alginate | 15 | — | HPMC (10%), Talc (200%) | 49 | — | 72 agglomeration of pellets | Fails |
| 4C | — | Potassium Alginate | 30 | — | Polyplasdone XL (25%), Talc (200%) | 19 | — | 58 agglomeration & gelling of pellets | Fails |
| 5C | — | Potassium Alginate | 25 | — | Polyplasdone XL (35%), TGalylcce (200%), Polysorbate 80 (2%) | 15 | — | 60 agglomeration & gelling of pellets | Fails |
| 6C | — | Sodium Alginate | 70 | — | Glycerine (15%), Talc(50%) | 86 | — | — | Fails |
| 7C | — | Sodium Alginate | 180 | — | Talc (50%) | 50 | — | 77 agglomeration of pellets | Fails |
| 8C | — | NM3OD: Sodium Alginate | 100 | 1:3 | Talc (50%) | 51 | — | 77 | Fails |
| 9C | — | L 30D 55: Sodium Alginate | 140 | 1:1.5 | Talc (50%) | 44 | — | 85 | Fails |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/ failed |
| 5C | — | — | — | — | — | — | — | — | — |
| 6C | — | — | — | — | — | — | — | — | — |
| 7C | — | — | — | — | — | — | — | — | — |
| 8C | — | — | — | — | — | — | — | — | — |
| 9C | 28 | 20 | 8 | 1 | — | — | — | — | Fails |

| | | | Amount | | | API Release | | | |
|---|---|---|---|---|---|---|---|---|---|
| Example No. | Inner/ Outer layer | Polymer Coating Type | Polymer Coating [%] | Ratio | Other excipients | Enteric pH 1.2 - 120 min | Buffer pH 5.5 45 min | Buffer pH 6.8 45 min | passed/ failed |
| 10C | — | L 30D 55:Sodium Alginate | 125 | 1:0.5 | Talc (50%),TEC(5%) | 20 | — | 77 | Fails |
| 11C | — | L 30D 55 | 20 | — | Talc (50%), TEC (10%) | 0 | — | 95 | Passes |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/ failed |
| 10C | 15 | 17 | 20 | 18 | — | — | — | — | Fails |
| 11C | 2 | 9 | 52 | 99 | — | — | — | — | Fails |

CAFFEINE PELLETS

| Example No. | Polymer Coating Type | Amount Polymer Coating [%] | Other excipients | API Release pH 1.2 + EtOH/ 120 min Enteric pH 1.2 - 120 min | passed/ failed |
|---|---|---|---|---|---|
| 12C | Sodium Alginate | 75 | Talc 50% | 94 | Fails |
| 13C | Sodium Alginate | 55 | Talc 50% | 97 | Fails |
| 14C | Sodium Alginate | 10 | Talc 50% | 93 | Fails |

| | API Release pH 1.2 + EtOH/120 min | | | | |
|---|---|---|---|---|---|
| Example No. | 5% EtOH | 10% EtOH | 20% EtOH | 40% EtOH | passed/ failed |
| 12C | 94 | 91 | 70 | 14 | Fails |
| 13C | — | — | — | 59 | Fails |
| 14C | — | — | — | 94 | Fails |

| Example No. | Inner/ Outer layer | Polymer Coating Type | Amount Polymer Coating [%] | Amount Polymer Coating (mg/cm²) | Ratio Outer/ Inner Coating | Other excipients | API Release Enteric pH 1.2 - 120 min | Buffer pH 5.5 45 min | Buffer pH 6.8 45 min | passed/ failed |
|---|---|---|---|---|---|---|---|---|---|---|
| 15 | Inner layer | Sodium alginate | 75 | 30 | 13.33 | Talc 50% | 0 | 94 | 100 | Passes |
| | Outer layer | L30D 55 | 10 | 4 | | Talc 50%, TEC 10% | | | | |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/ failed |
| 15 | 0 | 0 | 3 | 2 | 100 | 100 | 100 | 89 | Passes |

| | API Release Calcium - Tests | | | |
|---|---|---|---|---|
| Example No. | HCl + Ca pH 1.2/ 120 min | subsequent buffer pH 6.8 with Ca/ 45 min | subsequent buffer pH 6.8 without Ca/ 45 min | passed/ failed |
| 15 | 0 | 93 | 94 | Passes |

| Example No. | Inner/ Outer layer | Polymer Coating Type | Amount Polymer Coating [%] | Amount Polymer Coating (mg/cm²) | Ratio Outer/ Inner Coating | Other excipients | API Release Enteric pH 1.2 - 120 min | Buffer pH 5.5 45 min | Buffer pH 6.8 45 min | passed/ failed |
|---|---|---|---|---|---|---|---|---|---|---|
| 16 | Inner layer | Sodium alginate | 55 | 22 | 36.36 | Talc 50% | 0 | 95 | 97 | passes |
| | Outer layer | L 30D 55 | 20 | 8 | | Talc 50%, TEC 10% | | | | |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/ failed |
| 16 | 0 | 0 | 1 | 4 | 96 | 94 | 93 | 85 | Passes |

| | CAFFEINE PELLETS | | | |
|---|---|---|---|---|
| | API Release Calcium - Tests | | | |
| Example No. | HCl + Ca pH 1.2/ 120 min | subsequent buffer pH 6.8 with Ca/ 45 min | subsequent buffer pH 6.8 without Ca/ 45 min | passed/ failed |
| 16 | 0 | 98 | 96 | Passes |

| | | | | | | | API Release | | | |
|---|---|---|---|---|---|---|---|---|---|---|
| Example No. | Inner/ Outer layer | Polymer Coating Type | Amount Polymer Coating [%] | Amount Polymer Coating (mg/cm²) | Ratio Outer/ Inner Coating | Other excipients | Enteric pH 1.2 - 120 min | Buffer pH 5.5 45 min | Buffer pH 6.8 45 min | passed/ failed |
| 17 | Inner layer | Sodium alginate | 10 | 4 | 700 | Talc 50% | 0 | 0 | 90 | Passes |
| | Outer layer | L 30D 55 | 70 | 28 | | Talc 50%, TEC 10% | | | | |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/ failed |
| 17 | 0 | 0 | 0 | 6 | 88 | 89 | 97 | 82 | Passes |

| | API Release Calcium - Tests | | | |
|---|---|---|---|---|
| Example No. | HCl + Ca pH 1.2/ 120 min | subsequent buffer pH 6.8 with Ca/ 45 min | subsequent buffer pH 6.8 without Ca/ 45 min | passed/ failed |
| 17 | 0 | 87 | 91 | Passes |

| | | | | | | | API Release | | | |
|---|---|---|---|---|---|---|---|---|---|---|
| Example No. | Inner/ Outer layer | Polymer Coating Type | Amount Polymer Coating [%] | Amount Polymer Coating (mg/cm²) | Ratio Outer/ Inner Coating | Other excipients | Enteric pH 1.2 - 120 min | Buffer pH 5.5 45 min | Buffer pH 6.8 45 min | passed/ failed |
| 18 | Inner layer | Sodium alginate | 30 | 12 | 133.34 | Talc 50% | 0 | 80 | 89 | Passes |
| | Outer layer | L 30D 55 | 40 | 16 | | Talc 50%, TEC 10% | | | | |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/ failed |
| 18 | 0 | 0 | 0 | 6 | 88 | 89 | 93 | 84 | Passes |

| | API Release Calcium - Tests | | | |
|---|---|---|---|---|
| Example No. | HCl + Ca pH 1.2/ 120 min | subsequent buffer pH 6.8 with Ca/ 45 min | subsequent buffer pH 6.8 without Ca/ 45 min | passed/ failed |
| 18 | 0 | 89 | 87 | Passes |

| | | | | | | | API Release | | | |
|---|---|---|---|---|---|---|---|---|---|---|
| Example No. | Inner/ Outer layer | Polymer Coating Type | Amount Polymer Coating [%] | Amount Polymer Coating (mg/cm²) | Ratio Outer/ Inner Coating | Other excipients | Enteric pH 1.2 - 120 min | Buffer pH 5.5 45 min | Buffer pH 6.8 45 min | passed/ failed |
| 19 | Inner layer | Sodium alginate | 75 | 30 | 26.67 | Talc 50% | 0 | 94 | 95 | Passes |
| | Outer layer | HPMC AS LF | 20 | 8 | | Talc 30%, TEC 20% | | | | |

CAFFEINE PELLETS

SLS 3%

| Example No. | API Release pH 1.2 + EtOH/120 min | | | | API Release pH 1.2 + EtOH/120 min with subsequent buffer pH 6.8/45 min without EtOH | | | | passed/ failed |
|---|---|---|---|---|---|---|---|---|---|
| | 5% EtOH | 10% EtOH | 20% EtOH | 40% EtOH | 5% EtOH | 10% EtOH | 20% EtOH | 40% EtOH | |
| 19 | 0 | 0 | 8 | 2 | 95 | 97 | 96 | 78 | Passes |

| Example No. | API Release Calcium - Tests | | | passed/ failed |
|---|---|---|---|---|
| | HCl + Ca pH 1.2/ 120 min | subsequent buffer pH 6.8 with Ca/ 45 min | subsequent buffer pH 6.8 without Ca/ 45 min | |
| 19 | 0 | 95 | 93 | Passes |

| Example No. | Inner/ Outer layer | Polymer Coating Type | Amount Polymer Coating [%] | Amount Polymer Coating (mg/cm²) | Ratio Outer/ Inner Coating | Other excipients | API Release | | | passed/ failed |
|---|---|---|---|---|---|---|---|---|---|---|
| | | | | | | | Enteric pH 1.2 - 120 min | Buffer pH 5.5 45 min | Buffer pH 6.8 45 min | |
| 20 | Inner layer | Sodium alginate | 75 | 30 | 13.33 | Talc 50% | 0 | 91 | 97 | Passes |
| | Outer layer | L100 55 | 10 | 4 | | Talc 50%, TEC 10% | | | | |

| Example No. | API Release pH 1.2 + EtOH/120 min | | | | API Release pH 1.2 + EtOH/120 min with subsequent buffer pH 6.8/45 min without EtOH | | | | passed/ failed |
|---|---|---|---|---|---|---|---|---|---|
| | 5% EtOH | 10% EtOH | 20% EtOH | 40% EtOH | 5% EtOH | 10% EtOH | 20% EtOH | 40% EtOH | |
| 20 | 0 | 1 | 4 | 2 | 97 | 94 | 96 | 79 | Passes |

| Example No. | API Release Calcium - Tests | | | passed/ failed |
|---|---|---|---|---|
| | HCl + Ca pH 1.2/ 120 min | subsequent buffer pH 6.8 with Ca/ 45 min | subsequent buffer pH 6.8 without Ca/ 45 min | |
| 20 | 0 | 97 | 98 | Passes |

| Example No. | Inner/ Outer layer | Polymer Coating Type | Amount Polymer Coating [%] | Amount Polymer Coating (mg/cm²) | Ratio Outer/ Inner Coating | Other excipients | API Release | | | passed/ failed |
|---|---|---|---|---|---|---|---|---|---|---|
| | | | | | | | Enteric pH 1.2 - 120 min | Buffer pH 5.5 45 min | Buffer pH 7.5 45 min | |
| 21 | Inner layer | Sodium alginate | 75 | 30 | 13.33 | Talc 50% | 0 | — | 89 | Passes |
| | Outer layer | FS 30D | 10 | 4 | | Talc 50%, TEC 5% | | | | |

| Example No. | API Release pH 1.2 + EtOH/120 min | | | | API Release pH 1.2 + EtOH/120 min with subsequent buffer pH 7.5/45 min without EtOH | | | | passed/ failed |
|---|---|---|---|---|---|---|---|---|---|
| | 5% EtOH | 10% EtOH | 20% EtOH | 40% EtOH | 5% EtOH | 10% EtOH | 20% EtOH | 40% EtOH | |
| 21 | 0 | 0 | 0 | 0 | 89 | 88 | 82 | 88 | Passes |

CAFFEINE PELLETS

API Release Calcium - Tests

| Example No. | HCl + Ca pH 1.2/ 120 min | subsequent buffer pH 7.5 with Ca/ 45 min | subsequent buffer pH 7.5 without Ca/ 45 min | passed/ failed |
|---|---|---|---|---|
| 21 | 0 | 94 | 94 | Passes |

| Example No. | Inner/ Outer layer | Polymer Coating Type | Amount Polymer Coating [%] | Amount Polymer Coating (mg/cm²) | Ratio Outer/ Inner Coating | Other excipients | API Release Enteric pH 1.2 - 120 min | API Release Buffer pH 5.5 45 min | API Release Buffer pH 7.5 45 min | passed/ failed |
|---|---|---|---|---|---|---|---|---|---|---|
| 22C | — | FS 30D | 10 | 4 | — | Talc 50% TEC 5% | 0 | — | — | passes |

| | API Release pH 1.2 + EtOH/120 min | | | | API Release pH 1.2 + EtOH/120 min with subsequent buffer pH 7.5/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/ failed |
| 22C | 4 | 1 | 0 | 100 | — | — | — | — | Fails |

| Example No. | Inner/ Outer layer | Polymer Coating Type | Amount Polymer Coating % | Amount Polymer Coating (mg/cm²) | Ratio Outer/ Inner Coating | Other excipients | API Release Enteric pH 1.2 - 120 min | API Release Buffer pH 5.5 45 min | API Release Buffer pH 6.8 45 min | passed/ failed |
|---|---|---|---|---|---|---|---|---|---|---|
| 23 | Inner layer | Potassium alginate | 50 | 20 | 20 | Talc 50% | 0 | — | 76 | Passes |
|  | Outer layer | L 30D 55 | 10 | 4 |  | Talc 50%, TEC 10% |  |  |  |  |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/ failed |
| 23 | 2 | 8 | 8 | 2 | — | — | — | — | Passes |

API Release Calcium - Tests

| Example No. | HCl + Ca pH 1.2/ 120 min | subsequent buffer pH 6.8 with Ca/ 45 min | subsequent buffer pH 6.8 without Ca/ 45 min | passed/ failed |
|---|---|---|---|---|
| 23 | 0 | 83 | 79 | Passes |

| Example No. | Inner/ Outer layer | Polymer Coating Type | Amount Polymer Coating % | Amount Polymer Coating (mg/cm²) | Ratio Outer/ Inner Coating | Other excipients | API Release Enteric pH 1.2 - 120 min | API Release Buffer pH 5.5 45 min | API Release Buffer pH 6.8 45 min | passed/ failed |
|---|---|---|---|---|---|---|---|---|---|---|
| 24 | Inner layer | Ammonium alginate | 55 | 22 | 27.27 | Talc 50% | 0 | 96 | 85 | Passes |
|  | Outer layer | L 30D 55 | 15 | 6 |  | Talc 50%, TEC 10% |  |  |  |  |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/ failed |
| 24 | 0 | 0 | 2 | 7 | 93 | 92 | 95 | 89 | Passes |

CAFFEINE PELLETS

API Release Calcium - Tests

| Example No. | HCl + Ca pH 1.2/ 120 min | subsequent buffer pH 6.8 with Ca/ 45 min | subsequent buffer pH 6.8 without Ca/ 45 min | passed/ failed |
| --- | --- | --- | --- | --- |
| 24 | 0 | 91 | 86 | Passes |

| Example No. | Inner/ Outer layer | Polymer Coating Type | Amount Polymer Coating [%] | Amount Polymer Coating (mg/cm$^2$) | Ratio Outer/ Inner Coating | Other excipients | API Release Enteric pH 1.2 - 120 min | API Release Buffer pH 5.5 45 min | API Release Buffer pH 6.8 45 min | passed/ failed |
| --- | --- | --- | --- | --- | --- | --- | --- | --- | --- | --- |
| 25 | Inner layer | Sodium alginate | 55 | 22 | 18.18 | Talc 50% | 0 | 4 | 94 | Passes |
|    | Outer layer | Modified L 30D 55 | 10 | 4 |  | Talc 50%, TEC 10% |  |  |  |  |

| | API Release pH 1.2 + EtOH/120 min | | | | API Release pH 1.2 + EtOH/120 min with subsequent buffer pH 6.8/45 min without EtOH | | | | |
| --- | --- | --- | --- | --- | --- | --- | --- | --- | --- |
| Example No. | 5% EtOH | 10% EtOH | 20% EtOH | 40% EtOH | 5% EtOH | 10% EtOH | 20% EtOH | 40% EtOH | passed/ failed |
| 25 | 0 | 0 | 0 | 0 | 98 | 100 | 96 | 83 | Passes |

API Release Calcium - Tests

| Example No. | HCl + Ca pH 1.2/ 120 min | subsequent buffer pH 6.8 with Ca/ 45 min | subsequent buffer pH 6.8 without Ca/ 45 min | passed/ failed |
| --- | --- | --- | --- | --- |
| 25 | 0 | 94 | 98 | Passes |

LANSOPRAZOLE PELLETS

| Example No. | Inner/ Outer layer | Polymer Coating Type | Amount Polymer Coating [%] | Amount Polymer Coating (mg/cm$^2$) | Ratio Outer/ Inner Coating | Other excipients | API Release Enteric pH 1.2- 60 min | API Release Buffer pH 5.5 45 min | API Release Buffer pH 6.8 45 min | passed/ failed |
| --- | --- | --- | --- | --- | --- | --- | --- | --- | --- | --- |
| 26C | Inner layer | Sodium alginate | 40 | 16 | 25 | Talc 50% | 3 | 98 | 100 | Passes |
|     | Outer layer | L 30D 55 | 10 | 4 |  | Talc 50%, TEC 10% |  |  |  |  |

| | API Release pH 1.2 + EtOH/120 min | | | | API Release pH 1.2 + EtOH/60 min with subsequent buffer pH 6.8/45 min without EtOH | | | | |
| --- | --- | --- | --- | --- | --- | --- | --- | --- | --- |
| Example No. | 5% EtOH | 10% EtOH | 20% EtOH | 40% EtOH | 5% EtOH | 10% EtOH | 20% EtOH | 40% EtOH | passed/ failed |
| 26C | 0 | 0 | 0 | 1 | — | — | — | — | Passes |

API Release Calcium - Tests

| Example No. | HCl + Ca pH 1.2/ 60 min | subsequent buffer pH 6.8 with Ca/ 45 min | subsequent buffer pH 6.8 without Ca/ 45 min | passed/ failed |
| --- | --- | --- | --- | --- |
| 26C | 0 | 52 | 92 | Fails |

-continued

LANSOPRAZOLE PELLETS

| Example No. | Inner/ Outer layer | Polymer Coating Type | Amount Polymer Coating [%] | Amount Polymer Coating (mg/cm²) | Ratio Outer/ Inner Coating | Other excipients | API Release Enteric pH 1.2 - 60 min | API Release Buffer pH 5.5 45 min | API Release Buffer pH 6.8 45 min | passed/ failed |
|---|---|---|---|---|---|---|---|---|---|---|
| 27 | Inner layer | Sodium alginate | 40 | 16 | 50 | Talc 50% | 0 | 100 | 91 | Passes |
|  | Outer layer | L 30D 55 | 20 | 8 |  | Talc 50%, TEC 10% |  |  |  |  |

| Example No. | API Release pH 1.2 + EtOH/120 min 5% EtOH | 10% EtOH | 20% EtOH | 40% EtOH | API Release pH 1.2 + EtOH/60 min with subsequent buffer pH 6.8/45 min without EtOH 5% EtOH | 10% EtOH | 20% EtOH | 40% EtOH | passed/ failed |
|---|---|---|---|---|---|---|---|---|---|
| 27 | 0 | 0 | 0 | 0 | — | — | — | — | Passes |

| Example No. | API Release Calcium - Tests HCl + Ca pH 1.2/ 60 min | subsequent buffer pH 6.8 with Ca/ 45 min | subsequent buffer pH 6.8 without Ca/ 45 min | passed/ failed |
|---|---|---|---|---|
| 27 | 0 | 95 | 100 | Passes |

| Example No. | Inner/ Outer layer | Polymer Coating Type | Amount Polymer Coating [%] | Ratio Outer/ Inner Coating | Other excipients | API Release Enteric pH 1.2 - 120 min | API Release Buffer pH 5.5 45 min | API Release Buffer pH 6.8 45 min | passed/ failed |
|---|---|---|---|---|---|---|---|---|---|
| 28C | Inner layer | Neutralised L100 55 (neutralised to pH 6.0) | 5 | — | Talc 50% TEC 10% | 1 | — | — | Passes |
|  | Outer layer | L 30D 55 | 30 |  | Talc 50%, TEC 10% |  |  |  |  |

| Example No. | API Release pH 1.2 + EtOH/60 min 5% EtOH | 10% EtOH | 20% EtOH | 40% EtOH | API Release pH 1.2 + EtOH/120 min with subsequent buffer pH 6.8/45 min without EtOH 5% EtOH | 10% EtOH | 20% EtOH | 40% EtOH | passed/ failed |
|---|---|---|---|---|---|---|---|---|---|
| 28C | 1 | 1 | 1 | 87 | — | — | — | — | Fails |

CAFFEINE PELLETS

| Example No. | Inner/ Outer layer | Polymer Coating Type | Amount Polymer Coating [%] | Ratio Inner/ Outer Coating | Other excipients | API Release Enteric pH 1.2-120 min | API Release Buffer pH 5.5 45 min | API Release Buffer pH 6.8 45 min | passed/ failed |
|---|---|---|---|---|---|---|---|---|---|
| 29C | Inner layer | Neutralised L30D 55 (neutralised to pH 6.0) + 20% Citric acid | 5 | — | Talc 50% TEC 10% | 9 | — | 100 | Passes |

CAFFEINE PELLETS

| | | | | | |
|---|---|---|---|---|---|
| Outer layer | L 30D 55 | 10 | | Talc 50%, TEC 10% | |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/ failed |
| 29C | 17 | 17 | 45 | 100 | — | — | — | — | Fails |

METOPROLOL SUCCINATE PELLETS

| Example No. | Polymer Coating Type | Amount Polymer Coating [%] | Other excipients | API Release pH 1.2 + EtOH/ 120 min 40% EtOH | passed/ failed |
|---|---|---|---|---|---|
| 30C | Sodium Alginate | 75 | Talc 50% | 84 | Fails |
| 31C | Sodium Alginate | 100 | Talc 50% | 60 | Fails |
| 32C | Sodium Alginate | 120 | Talc 50% | 43 | Fails |

| Example No. | Inner/ Outer layer | Polymer Coating Type | Amount Polymer Coating [%] | Amount Polymer Coating (mg/cm$^2$) | Ratio Outer/ Inner Coating | Other excipients | API Release Enteric pH 1.2- 120 min | Buffer pH 5.5 45 min | Buffer pH 6.8 45 min | passed/ failed |
|---|---|---|---|---|---|---|---|---|---|---|
| 33C | Inner layer | Sodium alginate | 100 | 40 | 10 | Talc 50% | 0 | — | 99 | Passes |
| | Outer layer | L 30D 55 | 10 | 4 | | Talc 50%, TEC 10% | | | | |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/ failed |
| 33C | — | — | 48 | 1 | — | — | — | — | Fails |

| Example No. | Inner/ Outer layer | Polymer Coating Type | Amount Polymer Coating [%] | Amount Polymer Coating (mg/cm$^2$) | Ratio Outer/ Inner Coating | Other excipients | API Release Enteric pH 1.2-120 min | Buffer pH 5.5 45 min | Buffer pH 6.8 45 min | passed/ failed |
|---|---|---|---|---|---|---|---|---|---|---|
| 34 | Inner layer | Sodium alginate | 100 | 40 | 20 | Talc 50% | 0 | 98 | 100 | Passes |
| | Outer layer | L 30D 55 | 20 | 8 | | Talc 50%, TEC 10% | | | | |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/ failed |
| 34 | 0 | 0 | 0 | 0 | 100 | 100 | 98 | 81 | Passes |

METOPROLOL SUCCINATE PELLETS

API Release Calcium - Tests

| Example No. | HCl + Ca pH 1.2/ 60 min | subsequent buffer pH 6.8 with Ca/ 45 min | subsequent buffer pH 6.8 without Ca/ 45 min | passed/ failed |
|---|---|---|---|---|
| 34 | 0 | 98 | 100 | passes |

| Example No. | Inner/ Outer layer | Polymer Coating Type | Amount Polymer Coating [%] | Amount Polymer Coating (mg/cm²) | Ratio Outer/ Inner Coating | Other excipients | API Release Enteric pH 1.2-120 min | API Release Buffer pH 5.5 45 min | API Release Buffer pH 6.8 45 min | passed/ failed |
|---|---|---|---|---|---|---|---|---|---|---|
| 35 | Inner layer | Sodium alginate | 75 | 30 | 26.67 | Talc 50% | 0 | 93 | 100 | Passes |
|    | Outer layer | L 30D 55 | 20 | 8 |  | Talc 50%, TEC 10% |  |  |  |  |

| Example No. | API Release pH 1.2 + EtOH/120 min 5% EtOH | 10% EtOH | 20% EtOH | 40% EtOH | API Release pH 1.2 + EtOH/120 min with subsequent buffer pH 6.8/45 min without EtOH 5% EtOH | 10% EtOH | 20% EtOH | 40% EtOH | passed/ failed |
|---|---|---|---|---|---|---|---|---|---|
| 35 | 2 | 0 | 6 | 5 | 100 | 100 | 98 | 85 | Passes |

API Release Calcium - Tests

| Example No. | HCl + Ca pH 1.2/ 120 min | subsequent buffer pH 6.8 with Ca/ 45 min | subsequent buffer pH 6.8 without Ca/ 45 min | passed/ failed |
|---|---|---|---|---|
| 35 | 0 | 100 | 97 | Passes |

CAFFEINE MINITABLETS

| Example No. | Inner/ Outer layer | Polymer Coating Type | Amount Polymer Coating [%] | Amount Polymer Coating (mg/cm²) | Ratio Outer/ Inner Coating | Other excipients | API Release Enteric pH 1.2-120 min | API Release Buffer pH 5.5 45 min | API Release Buffer pH 6.8 45 min | passed/ failed |
|---|---|---|---|---|---|---|---|---|---|---|
| 36 | Inner layer | Sodium alginate | 40 | 18 | 25 | Talc 50% | 38 | — | — | Passes |
|    | Outer layer | L 30D 55 | 10 | 6 |  | Talc 50%, TEC 10% | 0 | 91 | 95 |  |

| Example No. | Inner/ Outer layer | API Release pH 1.2 + EtOH/120 min 5% EtOH | 10% EtOH | 20% EtOH | 40% EtOH | API Release pH 1.2 + EtOH/ 120 min with subsequent buffer pH 6.8/45 min without EtOH 5% EtOH | 10% EtOH | 20% EtOH | 40% EtOH | passed/ failed |
|---|---|---|---|---|---|---|---|---|---|---|
| 36 | Inner layer | 30 | 23 | 16 | 4 | — | — | — | — | Passes |
|    | Outer layer | 0 | 0 | 0 | 0 | 98 | 100 | 98 | 97 |  |

API Release Calcium - Tests

| Example No. | HCl + Ca pH 1.2/ 120 min | subsequent buffer pH 6.8 with Ca/ 45 min | subsequent buffer pH 6.8 without Ca/ 45 min | passed/ failed |
|---|---|---|---|---|
| 36 | 0 | 85 | 90 | Passes |

CAFFEINE MINITABLETS

| Example No. | Inner/Outer layer | Polymer Coating Type | Amount Polymer Coating [%] | Amount Polymer Coating (mg/cm²) | Ratio Outer/Inner Coating | Other excipients | API Release Enteric pH 1.2-120 min | API Release Buffer pH 5.5 45 min | API Release Buffer pH 6.8 45 min | passed/failed |
|---|---|---|---|---|---|---|---|---|---|---|
| 37 | Inner layer | Sodium alginate | 25 | 12 | 60 | Talc 50% | 0 | 84 | 98 | Passes |
|  | Outer layer | L 30D 55 | 15 | 10 |  | Talc 50%, TEC 10% |  |  |  |  |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/failed |
| 37 | 0 | 0 | 0 | 0 | 97 | 95 | 98 | 98 | Passes |

| | API Release Calcium - Tests | | | |
|---|---|---|---|---|
| Example No. | HCl + Ca pH 1.2/120 min | subsequent buffer pH 6.8 with Ca/45 min | subsequent buffer pH 6.8 without Ca/45 min | passed/failed |
| 37 | 0 | 99 | 97 | Passes |

| Example No. | Inner/Outer layer | Polymer Coating Type | Amount Polymer Coating [%] | Amount Polymer Coating (mg/cm²) | Ratio Outer/Inner Coating | Other excipients | API Release Enteric pH 1.2-120 min | API Release Buffer pH 5.5 45 min | API Release Buffer pH 6.8 45 min | passed/failed |
|---|---|---|---|---|---|---|---|---|---|---|
| 38C | Inner layer | Sodium alginate | 40 | 18 | 10 | Talc 50% | 0 | 97 | 94 | Passes |
|  | Outer layer | L 30D 55 | 4 | 3 |  | Talc 50%, TEC 10% |  |  |  |  |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/failed |
| 38C | 0 | 1 | 2 | 1 | 97 | 96 | 96 | 97 | Passes |

| | API Release Calcium - Tests | | | |
|---|---|---|---|---|
| Example No. | HCl + Ca pH 1.2/120 min | subsequent buffer pH 6.8 with Ca/45 min | subsequent buffer pH 6.8 without Ca/45 min | passed/failed |
| 38C | 0 | 30 | 88 | Fails |

| Example No. | Inner/Outer layer | Polymer Coating Type | Amount Polymer Coating [%] | Amount Polymer Coating (mg/cm²) | Ratio Outer/Inner Coating | Other excipients | API Release Enteric pH 1.2-120 min | API Release Buffer pH 5.5 45 min | API Release Buffer pH 6.8 45 min | passed/failed |
|---|---|---|---|---|---|---|---|---|---|---|
| 39 | Inner layer | Sodium alginate | 40 | 18 | 17.50 | Talc 50% | 0 | 96 | 95 | Passes |
|  | Outer layer | L 30D 55 | 7 | 4 |  | Talc 50%, TEC 10% |  |  |  |  |

CAFFEINE MINITABLETS

| | API Release pH 1.2 + EtOH/120 min | | | | API Release pH 1.2 +EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/failed |
| 39 | 0 | 0 | 1 | 0 | 99 | 99 | 97 | 93 | Passes |

| | API Release Calcium - Tests | | | |
|---|---|---|---|---|
| Example No. | HCl + Ca pH 1.2/ 120 min | subsequent buffer pH 6.8 with Ca/ 45 min | subsequent buffer pH 6.8 without Ca/ 45 min | passed/failed |
| 39 | 0 | 93 | 91 | Passes |

CAFFEINE CAPSULES

| Example No. | Inner/Outer layer | Polymer Coating Type | Amount Polymer Coating [%] | Amount Polymer Coating (mg/cm²) | Ratio Outer/Inner Coating | Other excipients | Enteric pH 1.2-120 min | Buffer pH 5.5 45 min | Buffer pH 6.8 45 min | passed/failed |
|---|---|---|---|---|---|---|---|---|---|---|
| 40 | Inner layer | Sodium alginate | 5.17 | 6 | 96.13 | Talc 50% | 0 | 7 | 99 | Passes 6.8, Fails 5.5 |
| | Outer layer | L 30D 55 | 4.97 | 6 | | Talc 50%, TEC 10% | | | | |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/failed |
| 40 | 0 | 0 | 0 | 0 | — | — | — | — | Passes |

| | API Release Calcium - Tests | | | |
|---|---|---|---|---|
| Example No. | HCl + Ca pH 1.2/ 120 min | subsequent buffer pH 6.8 with Ca/ 45 min | subsequent buffer pH 6.8 without Ca/ 45 min | passed/failed |
| 40 | 0 | 89 | 97 | Passes |

| Example No. | Inner/Outer layer | Polymer Coating Type | Amount Polymer Coating [%] | Amount Polymer Coating (mg/cm²) | Ratio Outer/Inner Coating | Other excipients | Enteric pH 1.2-120 min | Buffer pH 5.5 45 min | Buffer pH 6.8 45 min | passed/failed |
|---|---|---|---|---|---|---|---|---|---|---|
| 41 | Inner layer | Sodium alginate | 5.17 | 6 | 15.47 | Talc 50% | 0 | 93 | 100 | Passes |
| | Outer layer | L 30D 55 | 0.8 | 1 | | Talc 50%, TEC 10% | | | | |

| | API Release pH 1.2 + EtOH/120 min | | | | API Release pH 1.2 + EtOH/120 min with subsequent buffer pH 6.8/45 min without EtOH | | | | |
|---|---|---|---|---|---|---|---|---|---|
| Example No. | 5% EtOH | 10% EtOH | 20% EtOH | 40% EtOH | 5% EtOH | 10% EtOH | 20% EtOH | 40% EtOH | passed/failed |
| 41 | 0 | 0 | 3 | 1 | 99 | 99 | 95 | 93 | Passes |

CAFFEINE CAPSULES

| Example No. | API Release Calcium - Tests | | | passed/failed |
|---|---|---|---|---|
| | HCl + Ca pH 1.2/ 120 min | subsequent buffer pH 6.8 with Ca/ 45 min | subsequent buffer pH 6.8 without Ca/ 45 min | |
| 41 | 0 | 97 | 95 | Passes |

| Example No. | Inner/Outer layer | Polymer Coating Type | Amount Polymer Coating [%] | Amount Polymer Coating (mg/cm$^2$) | Ratio Outer/Inner Coating | Other excipients | API Release Enteric pH 1.2-120 min | Buffer pH 5.5 45 min | Buffer pH 6.8 45 min | passed/failed |
|---|---|---|---|---|---|---|---|---|---|---|
| 42 | Inner layer | Sodium alginate | 3.5 | 4 | 22.86 | Talc 50% | 0 | 95 | 94 | Passes |
| | Outer layer | L 30D 55 | 0.8 | 1 | | Talc 50%, TEC 10% | | | | |

| Example No. | API Release pH 1.2 + EtOH/120 min | | | | API Release pH 1.2 + EtOH/120 min with subsequent buffer pH 6.8/45 min without EtOH | | | | passed/failed |
|---|---|---|---|---|---|---|---|---|---|
| | 5% EtOH | 10% EtOH | 20% EtOH | 40% EtOH | 5% EtOH | 10% EtOH | 20% EtOH | 40% EtOH | |
| 42 | 0 | 0 | 2 | 4 | 99 | 98 | 96 | 96 | passes |

| Example No. | API Release Calcium - Tests | | | passed/failed |
|---|---|---|---|---|
| | HCl + Ca pH 1.2/ 120 min | subsequent buffer pH 6.8 with Ca/ 45 min | subsequent buffer pH 6.8 without Ca/ 45 min | |
| 42 | 0 | 97 | 97 | Passes |

DULOXETINE PELLETS

| Example No. | Inner/Outer layer | Polymer Coating Type | Amount Polymer Coating [%] | Amount Polymer Coating (mg/cm$^2$) | Ratio Outer/Inner Coating | Other excipients | API Release Enteric pH 1.2-120 min | Buffer pH 5.5 1 hour 30 min | Buffer pH 6.8 1 hour 30 min | passed/failed |
|---|---|---|---|---|---|---|---|---|---|---|
| 43 | Inner layer | Sodium alginate | 60 | | 25 | Talc 50% | 1 | 61 | 91 | Passes 6.8, Fails 5.5 |
| | Outer layer | L 30D 55 | 15 | | | Talc 50%, TEC 10% | | | | |

| Example No. | API Release pH 1.2 + EtOH/120 min | | | | API Release pH 1.2 + EtOH/120 min with subsequent buffer pH 6.8/45 min without EtOH | | | | passed/failed |
|---|---|---|---|---|---|---|---|---|---|
| | 5% EtOH | 10% EtOH | 20% EtOH | 40% EtOH | 5% EtOH | 10% EtOH | 20% EtOH | 40% EtOH | |
| 43 | 2 | 0 | 0 | 3 | — | — | — | — | Passes |

| Example No. | API Release Calcium - Tests | | | passed/failed |
|---|---|---|---|---|
| | HCl + Ca pH 1.2/ 120 min | subsequent buffer pH 6.8 with Ca/1 hour 30 min | subsequent buffer pH 6.8 without Ca/ 1 hour 30 min | |
| 43 | 0 | 89 | 90 | Passes |

CAFFEINE TABLETS

| Example No. | Inner/Outer layer | Polymer Coating Type | Polymer Coating [%] | Polymer Coating (mg/cm²) | Outer/Inner Coating | Other excipients | API Release Enteric pH 1.2-120 min | API Release Buffer pH 5.5 45 min | API Release Buffer pH 6.8 45 min | passed/failed |
|---|---|---|---|---|---|---|---|---|---|---|
| 44 | Inner layer | Sodium alginate | 1.78 | 2 | 100 | Talc 50% | 0 | 35 | 88 | Passes in 6.8, Fails in 5.5 |
|  | Outer layer | L 30D 55 | 1.78 | 2 |  | Talc 50%, TEC 10% |  |  |  |  |

| Example No. | API Release pH 1.2 + EtOH/120 min 5% EtOH | 10% EtOH | 20% EtOH | 40% EtOH | API Release pH 1.2 + EtOH/120 min with subsequent buffer pH 6.8/45 min without EtOH 5% EtOH | 10% EtOH | 20% EtOH | 40% EtOH | passed/failed |
|---|---|---|---|---|---|---|---|---|---|
| 44 | 1 | 1 | 3 | 5 | 88 | 87 | 91 | 92 | Passes |

| Example No. | API Release Calcium - Tests HCl + Ca pH 1.2/120 min | subsequent buffer pH 6.8 with Ca/45 min | subsequent buffer pH 6.8 without Ca/45 min | passed/failed |
|---|---|---|---|---|
| 44 | 0 | 91 | 90 | Passes |

| Example No. | Inner/Outer layer | Polymer Coating Type | Polymer Coating [%] | Polymer Coating (mg/cm²) | Outer/Inner Coating | Other excipients | API Release Enteric pH 1.2-120 min | API Release Buffer pH 5.5 45 min | API Release Buffer pH 6.8 45 min | passed/failed |
|---|---|---|---|---|---|---|---|---|---|---|
| 45 | Inner layer | Sodium alginate | 1.78 | 2 | 100 | Talc 50% | 4 | 92 | 92 | Passes |
|  | Outer layer | L 30D 55 | 1.78 | 1 |  | Talc 50%, TEC 10% |  |  |  |  |

| Example No. | API Release pH 1.2 + EtOH/120 min 5% EtOH | 10% EtOH | 20% EtOH | 40% EtOH | API Release pH 1.2 + EtOH/120 min with subsequent buffer pH 6.8/45 min without EtOH 5% EtOH | 10% EtOH | 20% EtOH | 40% EtOH | passed/failed |
|---|---|---|---|---|---|---|---|---|---|
| 45 | 4 | 4 | 5 | 5 | 92 | 87 | 94 | 75 | Passes |

| Example No. | API Release Calcium - Tests HCl + Ca pH 1.2/120 min | subsequent buffer pH 6.8 with Ca/45 min | subsequent buffer pH 6.8 without Ca/45 min | passed/failed |
|---|---|---|---|---|
| 45 | 4 | 91 | 91 | Passes |

The invention claimed is:

1. A pharmaceutical or nutraceutical composition, comprising
   a) a core, comprising a pharmaceutical or a nutraceutical active ingredient,
   b) an inner coating layer comprising at least 30% by weight of a salt of alginic acid selected from the group consisting of sodium alginate, potassium alginate, magnesium alginate and lithium alginate and a mixture thereof and up to 60% by weight of a glidant and wherein said inner coating layer does not comprise ammonium alginate, and
   c) an outer coating layer comprising at least 30% by weight of a polymer or a copolymer comprising anionic side groups,
   wherein the anionic polymer or copolymer in the outer coating layer is selected from the group consisting of (meth)acrylate copolymers or hydroxypropylmethyl cellulose acetate succinate
   which is gastric resistant, and resistant against the influence of ethanol and the influence of calcium ions.

2. The pharmaceutical or nutraceutical composition according to claim 1, wherein the amount of the inner coating layer is equal or higher than the amount of the outer coating layer.

3. The pharmaceutical or nutraceutical composition according to claim 1, wherein, except for the inner coating layer and the outer coating layer, no further controlling layers are present which control the release the pharmaceutical or a nutraceutical active ingredient.

4. The pharmaceutical or nutraceutical composition according to claim 1, wherein the salt of alginic acid in the inner coating layer has a viscosity of 30 to 720 cP of a 1% aqueous solution based on weight/weight.

5. The pharmaceutical or nutraceutical composition according to claim 1, which is gastric resistant, and wherein the inner and/or the outer coating layer comprises up to 60% by weight of a pharmaceutical or nutraceutically acceptable excipient.

6. The pharmaceutical or nutraceutical composition according to claim 1, wherein the release of the pharmaceutical or nutraceutical active ingredient is not more than 10% under in-vitro conditions at pH 1.2 for 2 hours in a buffered medium according to USP with and without the addition of 40% v/v ethanol.

7. The pharmaceutical or nutraceutical composition according to claim 1, wherein the release of the pharmaceutical or nutraceutical active ingredient is not more than 10% under in-vitro conditions at pH 1.2 for 2 hours in a buffered medium according to USP with and without the addition of 1.25 mM calcium-ions.

8. The pharmaceutical or nutraceutical composition according to claim 1, wherein the release of the pharmaceutical or nutraceutical active ingredient is at least 75% under in-vitro conditions at pH 6.8 or at pH 7.5 for 45 min in a buffered medium according to USP.

9. The pharmaceutical or nutraceutical composition according to claim 1, wherein the release of the pharmaceutical or nutraceutical active ingredient is at least 60% under in-vitro conditions at pH 5.5 for 90 min in a buffered medium according to USP.

10. The pharmaceutical or nutraceutical composition according to claim 1, wherein the polymer or copolymer comprising anionic side groups in the outer coating layer comprises 25 to 95 by weight free-radical polymerized $C_1$- to $C_{18}$-alkyl esters of acrylic or of methacrylic acid and 75 to 5% by weight (meth)acrylate monomers comprising an anionic group.

11. The pharmaceutical or nutraceutical composition according to claim 1, which is gastric resistant and is a coated tablet, a coated minitablet, a coated pellet, a coated granule, a sachet, a capsule filled with coated pellets or with powder or with granules, or a coated capsule.

12. A process for producing the pharmaceutical or nutraceutical composition according to claim 1, comprising forming the core comprising the active ingredient by direct compression, compression of dry, wet or sintered granules, by extrusion and subsequent rounding off, by wet or dry granulation, direct pelleting or by binding powders onto active ingredient-free beads or neutral cores or active ingredient-containing particles and applying the inner coating layer and the outer coating layer in the form of an aqueous dispersion or an organic solution in a spray process or by fluidized bed spray granulation.

13. The pharmaceutical or nutraceutical composition according to claim 1, wherein said outer coating layer comprises at least 30% by weight of a polymer or a copolymer comprising anionic carboxyl side groups.

14. The pharmaceutical or nutraceutical composition according to claim 1, wherein
the composition is a coated pellet or coated granule with a size of from 50 to 1000 μm, having from 2 to 50 mg of the salt of alginic acid per square centimeter, or
the composition is a coated tablet, a coated minitablet, or a coated capsule with a size of greater than 1 and up to 25 mm, having from 0.5 to 10 mg of the salt of alginic acid per square centimeter.

15. The pharmaceutical or nutraceutical composition according to claim 1, wherein the release of the pharmaceutical or nutraceutical active ingredient is not more than 10% under in-vitro conditions at pH 1.2 for 2 hours in a buffered medium according to USP with and without the addition of 40% v/v ethanol, and with and without the addition of 1.25 mM calcium-ions.

16. The pharmaceutical or nutraceutical composition according to claim 14, wherein the release of the pharmaceutical or nutraceutical active ingredient is not more than 10% under in-vitro conditions at pH 1.2 for 2 hours in a buffered medium according to USP with and without the addition of 40% v/v ethanol, and with and without the addition of 1.25 mM calcium-ions.

17. A process for controlled release of a pharmaceutical or nutraceutical to a patient in need thereof comprising orally administering to a patient in need there of the pharmaceutical or nutraceutical composition according to claim 1.

* * * * *